(12) United States Patent
Lutchen et al.

(10) Patent No.: US 6,435,182 B1
(45) Date of Patent: Aug. 20, 2002

(54) ENHANCED VENTILATION WAVEFORM DEVICE

(75) Inventors: Kenneth R. Lutchen, Framingham; David W. Kaczka, South Boston; Bela Suki, Newton Upper Falls, all of MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 09/535,135

(22) Filed: Mar. 24, 2000

Related U.S. Application Data

(60) Provisional application No. 60/125,969, filed on Mar. 24, 1999.

(51) Int. Cl.$^7$ .............................................. A61M 16/00
(52) U.S. Cl. ............................ 128/204.21; 128/204.18; 128/200.24
(58) Field of Search ............................ 128/898, 200.24, 128/204.18, 204.21, 204.19, 204.2, 204.22–205.26

(56) References Cited

U.S. PATENT DOCUMENTS

| | | | | | |
|---|---|---|---|---|---|
| 4,393,869 | A | * | 7/1983 | Boyarsky et al. | 128/204.18 |
| 5,669,379 | A | * | 9/1997 | Somerson et al. | 128/204.21 |
| 5,735,267 | A | * | 4/1998 | Tobia | 128/204.21 |
| 5,927,274 | A | * | 7/1999 | Servidio et al. | 128/204.18 |

OTHER PUBLICATIONS

Béla Suki et al., "Pseudorandom Signals to Estimate Apparent Transfer and Coherence Functions of Nonlinear Systems: Applications to Respiratory Mechanics," *IEEE Transactions on Biomedical Engineering*, vol. 39, No. 11, Nov. 1992, pp. 1142–1151.

Kenneth R. Lutchen et al., "Low–frequency respiratory mechanics using ventilator–driven forced oscillations," *The American Physiological Society*, 1993, pp. 2549–2560.

A. Harf et al., "Mechanical Ventilation with Superimposed High Frequency Oscillation in the Normal Rat," *Respiration Physiology*, 1983, vol. 54, pp. 31–40.

Daniel Navajas et al., "Respiratory input impedance in anesthetized paralyzed patients," *The American Physiological Society*, 1990, pp. 1372–1379.

Kenneth R. Lutchen et al., "Optimal ventilation waveforms for estimating low–frequency respiratory impedance," *The American Physiological Society*, 1993, pp. 478–488.

Bassel Tawfik, "A Nonlinear Model of Respiratory Mechanics in Emphysematous Lungs," *Annals of Biomedical Engineering*, vol. 16, pp. 159–174, 1988.

(List continued on next page.)

*Primary Examiner*—Glenn K. Dawson
(74) *Attorney, Agent, or Firm*—Samuels, Gauthier & Stevens, LLP

(57) ABSTRACT

A novel ventilator waveform having an enhanced inspiratory flow pattern is ideally suited for determining an effective "inspiratory impedance" in ventilator-dependent patients, and/or patients with severe obstruction resulting in expiratory flow-limitation. This waveform is referred to herein as the "Enhanced Ventilator Waveform" (EVW). The EVW maintains ventilatory support while simultaneously providing an accurate and sensible assessment of the mechanical status of the lungs or total respiratory system. The EVW technique of the present invention ensures that normal (tidal) volume levels are delivered during each inspiration, and that expiration remains passive. Furthermore, accurate estimation of lung resistance and elastance is established for several frequencies surrounding the primary ventilator breathing rate. From the resistance and elastance data, the mean level and structural distribution of airway versus tissue constriction conditions in the lung can be inferred. Additionally, the distribution of delivered gas is more uniform (i.e, more beneficial to the patient) with the EVW, as compared to conventional waveforms.

38 Claims, 8 Drawing Sheets

OTHER PUBLICATIONS

J. Mead et al., "The Mechanical Properties of the Lungs in Emphysema," Unknown Journal, pp. 1005–1016 (accepted for publication Mar. 9, 1955).

Edward D. Michaelson et al., "Pulmonary Mechanics by Spectral Analysis of Forced Random Noise," *The Journal of Clinical Investigation,* vol. 56, Nov. 1975, pp. 1210–1230.

* cited by examiner

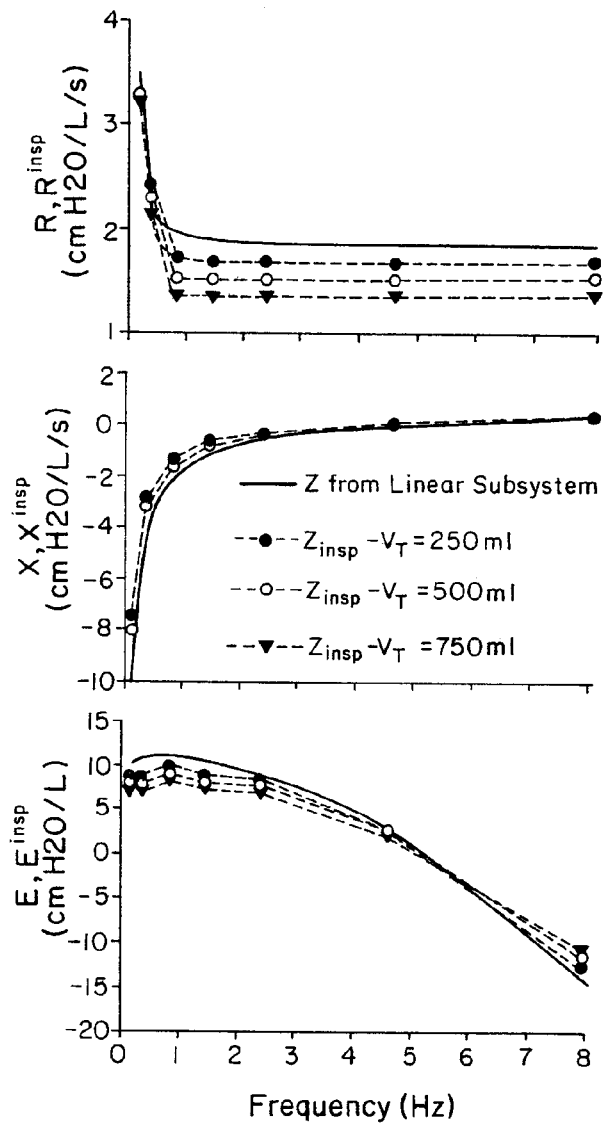 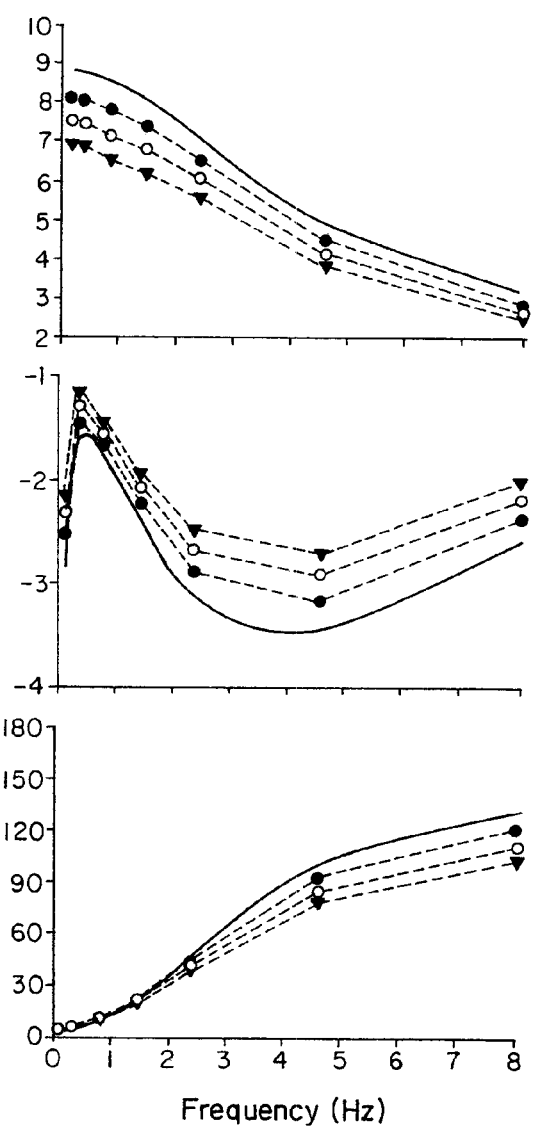
FIG. 6A    FIG. 6B

ENHANCED VENTILATION WAVEFORM DEVICE

RELATED APPLICATIONS

This application claims the benefit of U.S. Provisional Application Ser. No. 60/125,969, filed Mar. 24, 1999, the contents of which are incorporated by reference, in their entirety.

GOVERNMENT RIGHTS

This invention was made with Government Support under Contract Number BCS-9309426 awarded by the National Science Foundation and Contract Number HL50515-03 awarded by the National Institutes of Health. The Government has certain rights in the invention.

BACKGROUND OF THE INVENTION

For patients maintained on artificial mechanical ventilation, a primary concern of the clinician is the mechanical status of the lungs, which can often be inferred from estimates of total respiratory or pulmonary resistance (R) and elastance (E). Several techniques exist to assess R and E during mechanical ventilation at a given frequency, tidal volume, or mean airway pressure. Bates, J. H. T., and A. M. Lauzon, "A nonstatistical approach to estimating confidence intervals about model parameters: application to respiratory mechanics", IEES Trans. Biomed. Eng. 39: 94–100, 1992; Kaczka, D. W., G. M. Barnas, B. Suki, and K. R. Lutchen, "Assessment of time-domain analyses for estimation of low-frequency respiratory mechanical properties and impedance spectra", Ann. Biomed. Eng. 23: 135–151, 1995; Lutchen, K. R., D. W. Kaczka, B. Suki, G. Bamas, G. Cevenini, and P. Barbini, "Low-frequency respiratory mechanics using ventilator-driven forced oscillations"; J. Appl. Physiol. 75: 2549–2560, 1993; and Peslin, R., J. Felico de Silva, F. Chabot, and C. Duvivier, "Respiratory mechanics studied by multiple linear regression in unsedated ventilated patients", Eur. Respir. J. 5: 871–878, 1992.

Such estimates, however, do not permit inference on the level or distribution of obstruction in the airways, or the relative stiffness or viscance of the lung or respiratory tissues. Recent studies have suggested that the frequency dependence of R and E in breathing rates from 0.1 to 8 Hz embodies information needed to partition airway and tissue mechanical properties, or establish the dominant pattern of constriction in the airway tree. Petak, F., Z. Hantos, A. Adamicza, and B. Daroczy, "Partitioning of pulmonary impedance: modeling vs. alveolar capsule approach", J. Appl. Physiol. 75: 513–521, 1993; Lutchen, K. R., and H. Gillis, "Relationship between heterogeneous changes in airway morphometry and lung resistance and elastance", J. Appl. Physiol. 83: 1192–1201, 1997.

The frequency dependence of R and E can be derived from input impedance (Z), the complex ratio of pressure to flow during external forcing as a function of frequency. It is difficult to measure Z at low frequencies in ventilator-dependent patients, especially those with chronic obstructive pulmonary disease (COPD). Measurements relying on small-amplitude forced oscillations generated by loudspeakers require that the patient be disconnected from ventilatory support, which becomes impractical if low frequency information is desired, and becomes dangerous in patients with COPD. Navajas, D., R. Farre, J. Canet, M. Rotger, and J. Sanchis, "Respiratory input impedance in anesthetized paralyzed patients", J. Appl. Physiol. 69 1372–1379, 1990. Other investigators have used spectral analysis on standard volume-cycled ventilator waveforms to extract impedance information without disrupting mechanical ventilation (see Barnas, G. M., P. Harinath, M. D. Green, B. Suki, D. W. Kaczka, and K. R. Lutchen, "Influence of waveform and analysis technique on lung and chest wall properties", Respir. Physiol. 96: 331–344, 1994), but these attempts have been unsuccessful due to the waveforms' poor signal-to-noise ratio at harmonics above the frequency of ventilation as well as nonlinear harmonic distortion of the resulting pressure signal. Suki, B., and K. R. Lutchen, "Pseudorandom signals to estimate apparent transfer and coherence functions of nonlinear systems: applications to respiratory mechanics", IEEE Trans. Biomed. Eng. 39: 1142–1151, 1992 Recent studies have demonstrated that a broad-band Optimal Ventilator Waveform (OVW) can be used to measure Z in awake subjects with mild-to-moderate obstruction during tidal-like excursions with minimal harmonic distortion. Kaczka, D. W., E. P. Ingenito, B. Suki, and K. R. Lutchen, "Partitioning airway and lung tissue resistances in humans: effects of bronchoconstriction", J. Appl. Physiol. 82: 1531–1541, 1997; Lutchen, K. R., K. Yang, D. W. Kaczka, and B. Suki, "Optimal ventilation waveforms for estimating low-frequency respiratory impedance", J. Appl. Physiol. 75: 478–488, 1993. However the original OVW is oscillatory, which presents two problems. First, the active expiratory component of the OVW makes it impossible to use in patients whose obstruction may be so severe that their airways can be dynamically compressed during expiration. Mead, J., I. Lindgren, and E. A. Gaensler, "The mechanical properties of the lungs in emphysema", J. Clin. Invest. 34: 1005–1016, 1955. Second, it is generated via a closed system in which no fresh gas is delivered to the patient, and therefore long-term ventilation is impossible.

Besides the experimental limitations of measuring Z, an additional problem arises in its physical interpretation in patients with COPD. Regardless of the methods used to generate or acquire the data, Z has been computed using traditional spectral methods, which assume system linearity and time invariance. Daroczy, B., and Z. Hantos, "An improved forced oscillatory estimation of respiratory impedance", Int. J. Bio.-Med. Comput. 13: 221–235, 1982; Michaelson, E. D., E. D. Grassman, and W. Peters, "Pulmonary mechanics by spectral analysis of forced random noise", J. Clin. Invest. 56: 1210–1230, 1975. Depending on the patient's pathology, such assumptions can be grossly invalid. For example, the phenomena of dynamic airway compression and expiratory flow limitation are highly nonlinear processes, in which flow is no longer determined by the pressure drop across the airways. Fry, D. L., R. V. Ebert, W. W. Stead, and C. C. Brown, "The mechanics of pulmonary ventilation in normal subjects and in patients with emphysema", American Journal of Medicine 16: 80–97, 1954. In general, linear approximations in patients with severe obstruction must be restricted to data in which such processes are known to be absent, such as inspiration.

Current mechanical ventilators are operable in passive or active modes. With active modes, an effort by the patient triggers the delivery of a breath. With passive modes, only the ventilator is active and it delivers the breath at a pre-set breathing rate (frequency), volume per breath (tidal volume (VT)) and waveform. The most common active mode is referred to as volume support. With volume support, a pre-set flow wave shape is delivered via a ventilator pressure source during inspiration. Ventilator controlled solenoid valves then enable the patient to passively expire to the atmosphere. Current volume support waveforms include a)

a step to a constant flow rate (i.e. step waveform) delivered to produce the desired VT within the inspiratory time (TI); b) a ramp in which a peak flow is delivered immediately in the inspiration followed by a linear decrease in flow for the remainder of TI; and c) a sinusoid in which peak flow is reached proximal to the middle of inspiration.

The primary goal of all waveforms is to maintain blood gas levels ($O_2$ and $CO_2$) to sustain normoxia and nomocapnia. Because ventilation via pressure produced at the mouth is not natural, another requirement is that the ventilator not produce excessive pressure at the airway opening. This can lead to barotrauma (intralung airway damage), which in turn can cause respiratory distress.

During mechanical ventilation, the clinician is concerned (among other things) with the mechanical status of the patient. Specifically, it is desirable to estimate the degree of airway obstruction or constriction, the distribution of constriction in the airways, and the relative stiffness and viscosity of the lung tissues. This assessment can be made by examining the resistance R and elastance E at several frequencies surrounding normal breathing rates (i.e., from about 0.1–8 Hz). The behavior of the R and E spectra over this frequency range are very distinct for particular forms and degrees of lung disease. Such information is helpful in a) determining the severity of any lung disease that is present and its response to therapy and the mechanical ventilation itself; b) the pressures necessary at the airway opening to deliver a desired volume; and c) determining the likelihood of success in weaning the patient from the ventilator.

Current mechanical ventilation waveforms permit assessment of lung mechanical properties at only a single breathing rate, that of the ventilator itself. Knowledge of R and E at this particular frequency may be very misleading as to the mean level of airway resistance and the relative distribution of the disease among the airways and between the airways and tissues. Likewise, the waveform shapes available for volume ventilation are very limited and not optimized for a) minimizing airway pressures or b) maximizing ventilation distribution.

SUMMARY OF THE INVENTION

The present invention is directed to an apparatus and method that provides a novel ventilator waveform having an enhanced inspiratory flow pattern ideally suited for determining an effective "inspiratory impedance" in ventilator-dependent patients, and/or patients with severe obstruction resulting in expiratory flow-limitation. This waveform is referred to herein as the "Enhanced Ventilator Waveform" (EVW). In theory, the EVW will maintain ventilatory support while simultaneously providing an accurate and sensible assessment of the mechanical status of the lungs or total respiratory system. A technique for computing inspiratory impedance, for example a weighted-least-squares technique, is also provided.

The EVW technique of the present invention ensures that normal (tidal) volume levels are delivered during each inspiration, and that expiration remains passive. Furthermore, accurate estimation of lung resistance and elastance is established for several frequencies surrounding the primary ventilator breathing rate. From the resistance and elastance data, the mean level and structural distribution of airway versus tissue constriction conditions in the lung can be inferred. Additionally, the distribution of delivered gas is more uniform (i.e, more beneficial to the patient) with the EVW, as compared to conventional waveforms.

In a first embodiment, the method of the present invention is directed to a method for estimating the frequency dependence of respiratory impedance in a patient. A ventilation function is generated comprising an inspiratory waveform formed by a plurality of energy waves at predetermined frequencies. Flow and pressure data are estimated during delivery of the ventilation function to the patent. Flow and pressure waveforms are generated from the estimated flow and pressure data. Frequency components in the flow and pressure waveforms are calculated at each predetermined frequency. A respiratory impedance estimate is calculated at each predetermined frequency based on the flow and pressure waveforms.

In a preferred embodiment, the respiratory impedance estimate includes estimates of resistance and elastance components. Estimation of the flow and pressure data preferably comprises measuring pressure and flow data at the delivery apparatus delivering the ventilation function, or optionally, may comprise measuring pressure and flow data at the input to the respiratory system. The frequency components of the flow and pressure waveforms may comprise amplitude and phase.

In a preferred embodiment, the frequency components in the flow and pressure waveforms are calculated at each predetermined frequency using time-weighted linear regression, with calculations being performed in the time domain, and wherein the flow and pressure waveforms are time-domain waveforms. Each time-domain flow and pressure waveform may comprise a sum of sine waves of the predetermined frequencies.

The respiratory impedance estimate may be based on an impedance calculation at each predetermined frequency as a ratio of the pressure and flow waveforms. The frequencies may be selected according to no-sum-no-difference criteria. The energy waves may have magnitudes that are chosen to ensure sufficient signal-to-noise in the resulting estimate, and may have phases that are chosen such that the resulting ventilation function delivers sufficient fluid volume to maintain ventilation.

In a preferred embodiment the patient is isolated from the ventilation function to allow for natural expiration, with data being collected only during inspiration. Accordingly, the system may be configured to permit different inspiration and expiration time durations.

The predetermined frequencies are preferably within a range of 0.1 Hz and 8 Hz. High-frequency components may be applied to the ventilation function to provide for a therapeutic effect.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 6A and 6B are charts for comparison of $R^{insp}$, $X^{insp}$, and $E^{insp}$ spectra estimated from EVW data at tidal volumes of 250 ml (●), 500 ml (○), and 750 ml (♦), for the first and second models of FIG. 3 respectively, in accordance with the present invention.

DETAILED DESCRIPTION OF PREFERRED EMBODIMENTS

Figure 1:
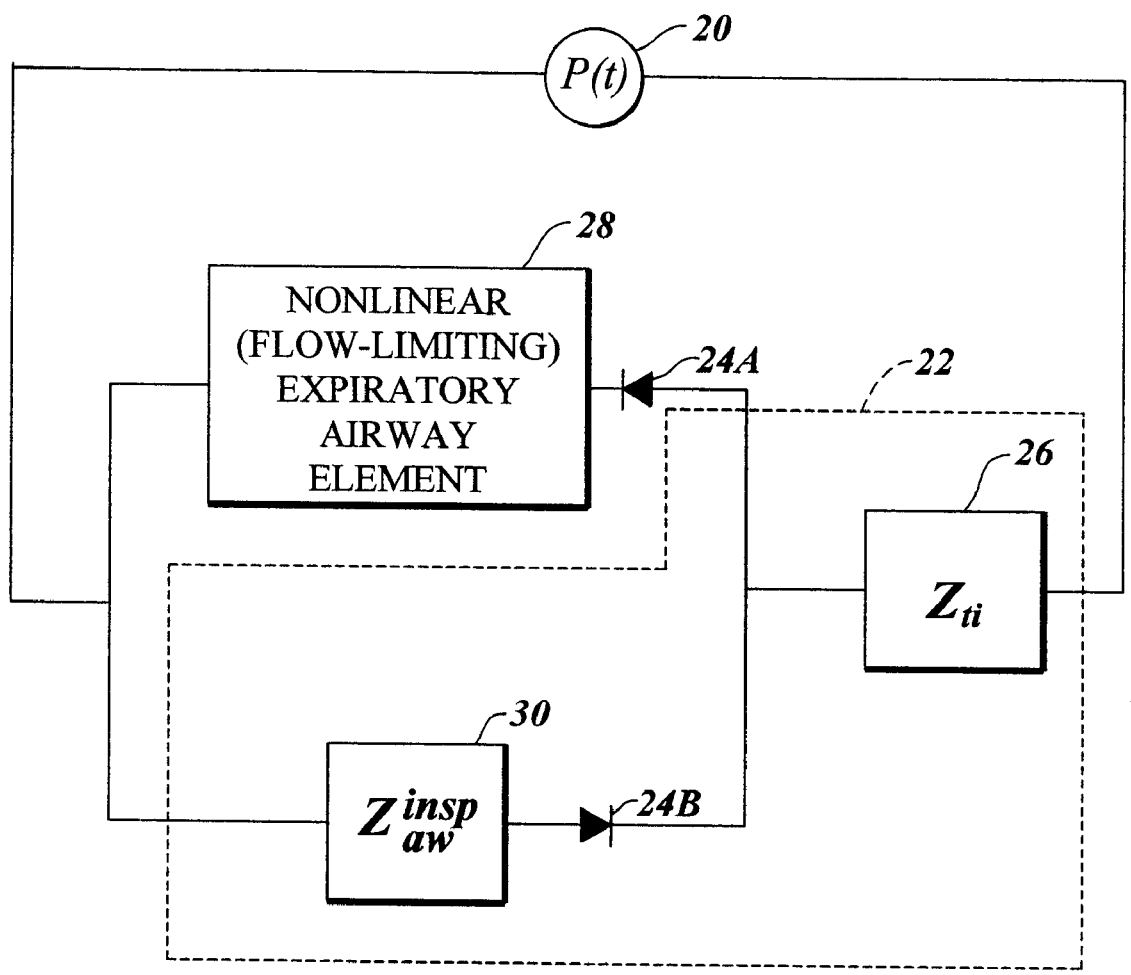
FIG. 1 is a block diagram of a simple respiratory model for flow-limited patients, consisting of a linear tissue element ($Z_{ti}$) as well as linear inspiratory ($Z_{aw}^{insp}$) and nonlinear expiratory airway elements, in accordance with the present invention.

The EVW of the present invention is a flow waveform and analysis approach that addresses the limitations of conventional techniques, while allowing for accurate assessment of resistance R and elastance E at breathing rates between 0.1–8 Hz. The EVW is fully compatible with modern ventilation technology. The waveform sustains ventilation by delivering the desired tidal volume, but actually contains energy at all frequencies of interest, even though the shape of the delivered volume is close to a typical breath. A novel feature of the present invention is that it allows for fresh gas to be provided at inspiration and allows for passive expiration.

Approximately the same total energy as a standard step ventilator waveform is utilized, but the energy is redistributed. The dominant energy is placed at the desired breathing frequency, and energy levels at other frequencies are increased to ensure sufficient signal-to-noise. Energy is not necessarily placed at all frequencies. In fact, frequencies are preferably selected via a no-sum-no-difference (NSND) criteria so that none of the frequencies is an integer multiple of another (ie., energy at any one input frequency cannot produce harmonic distortion at any other input frequencies) and so that none can be created by the sum and difference of "n" other frequencies. This condition ensures that the output pressure will be subject to a minimum influence of nonlinear distortions at any of the input frequencies. The delivered flow waveform during inspiration is the sum of the sine waves associated with the NSND frequencies in the waveform. The magnitudes and phases of the sine waves are optimized for a given patient to maximize the volume delivered while minimizing the peak-to-peak airway opening pressures. The resultant waveform, if delivered as-is, would be periodic and would require an active inspiration and expiration. However, a preferred embodiment of the present invention utilizes a pair of computer-controlled solenoid valves (common on standard ventilators) to deliver the EVW on inspiration only, thereby allowing the subject to passively expire to the atmosphere. In this manner, any subject, regardless of the degree of progression of lung disease, can be indefinitely supported by the ventilator-oscillator system.

Estimating R and E versus frequency (otherwise known as the lung impedance Z) from these new waveforms requires non-traditional signal processing. For conventional periodic signals, such as the OVW, one could simply calculate the ratio of the Fast Fourier Transform, FFT (a standard signal processing algorithm) of pressure to flow averaged over several overlapping time windows of equal length. With an EVW of the present invention, the expiration portion of the waveform is no longer frequency-optimized (i.e., it contains energy over a continuous spectrum). It has previously been shown that application of an FFT over a full standard ventilator breath will lead to spectral leakage and nonlinear spectral distortion. Lutchen, K. R, D. W. Kaczka, B. Suki, G. M. Barnas, G. Cevenini, and P. Barbini, "Low frequency respiratory mechanics using ventilator-driven forced oscillations", J. Appl. Physiol. 75(6): 2549–2560, 1993.

It is however possible to "spectrally analyze" only the inspiration portion of this waveform by taking advantage of a priori knowledge of its frequency content. Here the flow and pressure can be described as a trigonometric Fourier Series as shown below in Equation 1, where K is the number of frequencies in the waveform (for example 7–8) and $f_k$ are the known frequencies. A set of amplitudes are estimated (eg., $a_k$ and $b_k$ for the flow) by fitting this function to the sampled data via linear regression. The elegance of this approach arises from the fact that it is known that the time-domain waveforms are dominated by the NSND frequencies (for example, 7 or 8 precalculated known frequencies) all of which are minimally influenced by non-linearities. Hence, the "spectral" analysis can be limited to these frequencies only. This approach immediately provides an estimate of the $Z_L$ at these frequencies. For example, accurate estimates can be generated in as few as 6–8 breathing cycles. The EVW has extraordinary longterm potential for patient lung monitoring in an operating room, ICU or clinical environment. Additionally, because the EVW contains high frequency components, it is more conductive to enhancement of gas transport and ventilation distribution, as compared to conventional mechanical ventilation waveforms.

The new EVW through non-traditional signal analysis now represents a waveform fully compatible with modern ventilation technology. It is unique in several respects including a) signal design is compatible with ventilator solenoid timing to permit application only on inspiration; b) R and E can be estimated both above and below the ventilator breathing frequency; and c) the signal processing approach takes advantage of the NSND choice of frequencies so that a trigonometric Fourier series can be applied to the sampled time domain waveforms. The last point is particularly important, since standard methods to estimate R and E (i.e., FFTs) would not work.

Inspiratory Impedance

Even when the airway pressure-flow relationship is extremely nonlinear during expiration (see Dayman, H., "Mechanics of airflow in health and emphysema.", *J. Clin. Invest.* 30: 1175–1190, 1951; Mead et al. (1955) supra; and Tawfik, B., and H. K. Chang, "A nonlinear model of respiratory mechanics in emphysematous lungs", *Ann. Biomed Eng.* 16: 159–174, 1988), it is reasonably linear during inspiratory maneuvers provided peak flows and volume excursions are within normal physiological limits. Thus the tools of linear systems theory, such as impedance transfer function approximation, may still be employed provided the analysis is limited to this linear inspiratory region. In this sense, an effective "inspiratory impedance" ($Z^{insp}$) may be defined as that mechanical impedance offered by the respiratory system to a net inspiratory flow at the airway opening. The concept of $Z^{insp}$ in flow-limited patients can be better illustrated by considering the simplified respiratory model shown in FIG. 1.

FIG. 1 is a block diagram of a simple respiratory model for flow-limited patients, consisting of a linear tissue element ($Z_{ti}$) as well as linear inspiratory ($Z_{aw}^{insp}$) and nonlinear expiratory airway elements, in accordance with the present invention. In the diagram, P(t) 20 denotes either transrespiratory or transpulmonary pressure, and the portion enclosed by the dashed lines is the effective inspiratory impedance ($Z^{insp}$).

Here, two opposing check valves represented by diodes 24A, 24B separate a tissue impedance $Z_{ti}$ 26 from two separate airway systems 28, 30 in parallel. These systems 28, 30 do not represent two distinct anatomical pathways for air flow to and from the tissues; rather, they suggest the applicability of two distinct mathematical pressure-flow relationships for the airways. During inspiration, air flows into the tissues through a (presumed) linear airway system 30 with a characteristic mechanical impedance, $Z_{aw}^{insp}$. However during expiration, the air flows out of the alveoli through a nonlinear system 28 that can mimic flow limitation. For this model then, $Z^{insp}$ would be the series combination of the $Z_{aw}^{insp}$ and $Z_{ti}$ elements.

Note that the nonlinear expiratory airway element is not characterized with an apparent mechanical impedance, since this would imply a linear transfer relationship between its input (flow) and output (pressure). Although airways during inspiration are represented here as a simple one-port system, a two-port airway system with a shunt compliance to account for airway wall distensibility, is equally applicable.

The Enhanced Ventilator Waveform

Figure 2A:
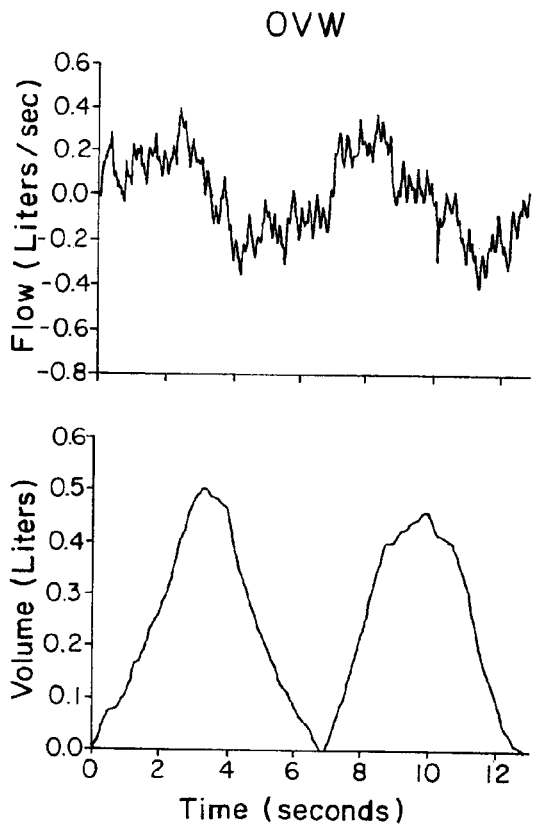
FIGS. 2A and 2B are exemplary charts of flow and volume tracings as functions of time for comparing the conventional Optimal Ventilator Waveform (OVW) and the Enhanced Ventilator Waveform (EVW) of the present invention.

Previous studies have relied on a broad-band Optimal Ventilator Waveform (OVW) to measure low frequency Z in human subjects, as explained above. The OVW contains energy concentrated at frequencies which obey the Non-Sum-Non-Difference (NSND) criteria (see Suki, B., and K. R. Lutchen, "Pseudorandom signals to estimate apparent transfer and coherence functions of nonlinear systems: applications to respiratory mechanics", *IEEE Trans. Biomed. Eng.* 39: 1142–1151, 1992), such that none of the frequencies are integer multiples of each other. The resulting pressure responses at those frequencies are therefore not distorted by harmonic distortion and minimally influenced by crosstalk arising from simple nonlinearities. In addition, the phases at each frequency in this waveform are optimized to ensure that physiological tidal-like excursions are delivered to the subject while peak airway pressures are minimized. A typical OVW is illustrated in FIG. 2A. This particular OVW contains energy from 0.15625 to 8.1 Hz. Its magnitudes and phases are presented in Table 1, which includes information related to the frequencies $f_k$, relative magnitudes, and phases for the OVW shown in FIG. 2A and the EVW shown in FIG. 2B, as well as the number oscillatory cycles of each $f_k$ per inspiratory period ($T_1$). Note that this data is provided by way of example only, and that the operation of the present invention is in now way limited to operations at these frequencies, or other parameters specified below.

TABLE 1

| $f_k$ (Hz) | Relative Magnitude | Phase (radians) | Cycles per $T_1$ |
|---|---|---|---|
| 0.156250 | 1.000 | 4.95 | 0.50 |
| 0.390625 | 0.300 | 3.82 | 1.25 |
| 0.859375 | 0.250 | 4.37 | 2.75 |
| 1.484375 | 0.250 | 3.67 | 4.75 |
| 2.421875 | 0.175 | 4.05 | 7.75 |
| 4.609375 | 0.175 | 4.13 | 14.75 |
| 8.046875 | 0.125 | 4.02 | 25.75 |

Note further that since the NSND criteria requires that no energy be placed at the fundamental frequency of the OVW, one full period of this waveform actually contains two distinct physiological breaths.

The OVW is useful for assessing pulmonary mechanics in awake subjects who can be trained to relax their chest wall muscles. However, it is unsuitable for use in ventilator dependent patients and/or patients with severe lung obstruction and flow limitation since it does not permit a passive expiration. Moreover, its periodic nature and bi-directional flows require it to be generated via a closed piston-cylinder system with no fresh gas delivered to the patient. Although the duration of a single measurement can be increased using an $O_2$ bias flow and/or a soda-lime scrubber, the longest a healthy awake subject can remain on such a system is approximately 90 seconds.

Figure 2B:
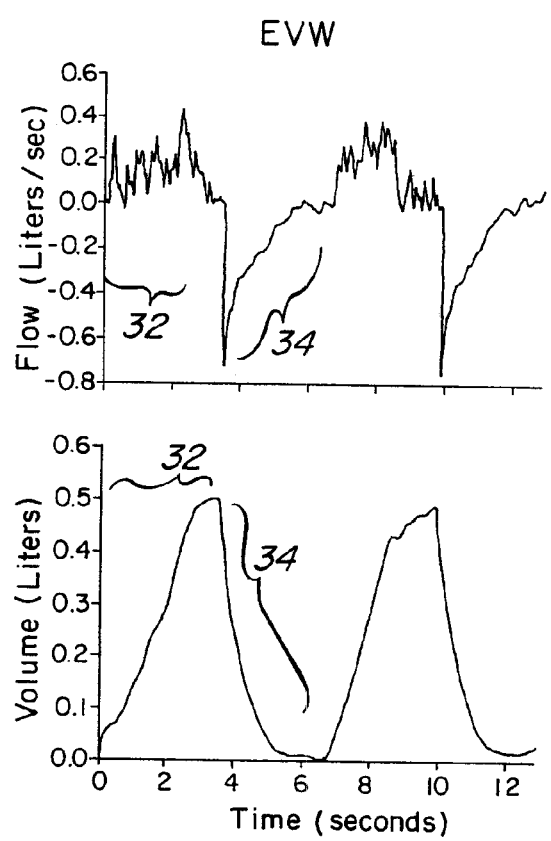

In accordance with the present invention, the Enhanced Ventilator Waveform (EVW) shown in FIG. 2B seeks to circumvent these drawbacks by: 1) sustaining mechanical ventilation with the delivery of an appropriate volume of fresh gas to the patient using an inspiratory flow pattern 32 identical to the OVW shown in FIG. 2A; and 2) allowing the patient to passively exhale to the atmosphere 34. As with the OVW, a preferred embodiment of this particular EVW contains two distinct physiological breaths per complete cycle.

Computing Inspiratory Impedance

The design of the EVW poses several challenges which preclude the application of traditional spectral methods to compute $Z^{insp}$. Unlike the OVW, the complete EVW cycle is not optimized to avoid simple nonlinearities even if flow limitation is absent; the passive expiratory portion of the waveform can cause harmonic distortions in the pressure waveform which will corrupt the resulting Z spectra computed from traditional spectral techniques. However, when one restricts analysis to inspiratory segments, additional problems become apparent. Each of the EVW sinusoids may not necessarily have an integer number of cycles over the inspiratory period $T_1$ (e.g., Table 1—above). This means that if a discrete Fourier transform (DFT) is taken only over the inspiratory period $T_1$, the frequency resolution may not correspond to any particular input frequency. Thus, spectral leakage with corresponding distortion of $Z^{insp}$ will occur.

An additional problem with traditional spectral approaches is the assumption that the system under analysis has achieved a dynamic oscillatory steady-state. In the case of the present invention, each EVW inspiration is preferably initiated when expiratory airflow has ceased and the lungs have achieved a near-static mechanical equilibrium with the chest wall and/or an externally applied positive end-expiratory pressure (PEEP). Hence the measured inspiratory flow and pressure segments following each expiration will consist of both transient and steady-state components. The transient components reflect various physical processes occurring in the lungs (i.e., stress-relaxation, pendulluft, alveolar recruitment, etc.), as well as the dynamic responses of any instrumentation used for data acquisition. Regardless of the source of these transients, they appear in the Fourier domain as a continuous distribution of frequencies and can introduce additional bias and distortion in estimates of $Z^{insp}$.

To avoid these problems and still obtain a reasonable estimate of the steady-state spectral content of the inspiratory flow and pressure segments, the approach of the present invention takes advantage of the a priori knowledge of the frequency distribution of the EVW inspiration (Table 1) and model both the flow and pressure with trigonometric approximations:

$$\dot{V}(t_n^m) = a_0 + \sum_{k=1}^{K} a_k \cos(2\pi f_k t_n^m) + \sum_{k=1}^{K} b_k \sin(2\pi f_k t_n^m) + \varepsilon_{\dot{V}}(t_n^m) \quad (1)$$

$$P(t_n^m) = c_0^i + \sum_{k=1}^{K} c_k \cos(2\pi f_k t_n^m) + \sum_{k=1}^{K} d_k \sin(2\pi f_k t_n^m) + \varepsilon_P(t_n^m) \quad (2)$$

where $t_n^m$ is the sampling index representing the time of the nth sample obtained during the mth inspiration, and the scaling coefficients $a_k$, $b_k$, $c_k$, and $d_k$ are real numbers that determine the linear, steady-state oscillatory response for flow and pressure at each specified frequency $f_k$. Note that since the mean value of the inspiratory pressure segment will be slightly different for each unique flow pattern presented to the respiratory system, Equation 2 will have a different DC component, $c_0^i$, for each unique EVW inspiration (in the preferred case, i=1,2). The error terms $\varepsilon_{\dot{V}}(t_n^m)$ and $\varepsilon_P(t_n^m)$ account for both observation and modeling error, and include contributions from random measurement noise, as well as deterministic components due to the transient responses, harmonic distortions, and cardiogenic oscillations. Equations 1 and 2 are not true trigonometric Fourier expansions of the inspiratory segments, since each $f_k$ is not required to be an integer multiple of $1/T_1$. Thus spectral leakage can be avoided. Note that the above approximation formulae are given by way of example, and other relationships may be equally applicable to the present invention.

Insofar as these trigonometric coefficients reflect the steady-state magnitudes and phases for the inspiratory flow and pressure segments, an effective $Z^{insp}$ can be computed at each discrete frequency as:

$$Z^{insp}(f_k) = \frac{c_k - jd_k}{a_k - jb_k} \quad (3)$$

from which inspiratory resistance ($R^{insp}$) and elastance ($E^{insp}$) can be estimated from the real (Re) and imaginary (Im) parts of $Z^{insp}$, respectively:

$$R^{insp}(f_k) = Re\{Z^{insp}(f_k)\} \quad (4)$$

$$E^{insp}(f_k) = -2\pi f_k Im\{Z^{insp}(f_k)\} \quad (5)$$

If a total of M inspirations are sampled with N flow and N pressure points per inspiratory period, two linear systems of MN equations can be obtained: one for flow (Equation 1) and one for pressure (Equation 2). Either system can be expressed in matrix notation as:

$$Y = X\Theta + \epsilon \quad (6)$$

where for flow, $$Y = [\dot{V}(t_1^1) \ \dot{V}(t_2^1) \ \ldots \ \dot{V}(t_N^1) | \ \ldots \ | \dot{V}(t_1^M) \ \dot{V}(t_2^M) \ \ldots \ \dot{V}(t_N^M)]^T$$

$$\Theta = [a_0 \ a_1 \ b_1 \ a_2 \ b_2 \ \ldots \ a_K \ b_K]^T$$

$$\epsilon = [\epsilon_{\dot{V}}(t_1^1) \ \epsilon_{\dot{V}}(t_2^1) \ \ldots \ \epsilon_{\dot{V}}(t_N^1) | \ \ldots \ | \epsilon_{\dot{V}}(t_1^M) \ \epsilon_{\dot{V}}(t_2^M) \ \ldots \ \epsilon_{\dot{V}}(t_N^M)]^T$$

$$X = \begin{bmatrix} 1 & \cos(2\pi f_1 t_1^1) & \sin(2\pi f_1 t_1^1) & \cos(2\pi f_2 t_1^1) & \sin(2\pi f_2 t_1^1) & \cdots & \cos(2\pi f_K t_1^1) & \sin(2\pi f_K t_1^1) \\ 1 & \cos(2\pi f_1 t_2^1) & \sin(2\pi f_1 t_2^1) & \cos(2\pi f_2 t_2^1) & \sin(2\pi f_2 t_2^1) & \cdots & \cos(2\pi f_K t_2^1) & \sin(2\pi f_K t_2^1) \\ \vdots & \vdots & \vdots & \vdots & \vdots & & \vdots & \vdots \\ 1 & \cos(2\pi f_1 t_N^1) & \sin(2\pi f_1 t_N^1) & \cos(2\pi f_2 t_N^1) & \sin(2\pi f_2 t_N^1) & \cdots & \cos(2\pi f_K t_N^1) & \sin(2\pi f_K t_N^1) \\ \vdots & \vdots & \vdots & \vdots & \vdots & & \vdots & \vdots \\ 1 & \cos(2\pi f_1 t_1^M) & \sin(2\pi f_1 t_1^M) & \cos(2\pi f_2 t_1^M) & \sin(2\pi f_2 t_1^M) & \cdots & \cos(2\pi f_K t_1^M) & \sin(2\pi f_K t_1^M) \\ 1 & \cos(2\pi f_1 t_2^M) & \sin(2\pi f_1 t_2^M) & \cos(2\pi f_2 t_2^M) & \sin(2\pi f_2 t_2^M) & \cdots & \cos(2\pi f_K t_2^M) & \sin(2\pi f_K t_2^M) \\ \vdots & \vdots & \vdots & \vdots & \vdots & & \vdots & \vdots \\ 1 & \cos(2\pi f_1 t_N^M) & \sin(2\pi f_1 t_N^M) & \cos(2\pi f_2 t_N^M) & \sin(2\pi f_2 t_N^M) & \cdots & \cos(2\pi f_K t_N^M) & \sin(2\pi f_K t_N^M) \end{bmatrix} \quad (7)$$

while for pressure, $$Y = [P(t_1^1) \ P(t_2^1) \ \ldots \ P(t_N^1) | \ \ldots \ | P(t_1^M) \ P(t_2^M) \ \ldots \ P(t_N^M)]^T$$

$$\Theta = [c_0^1 \ c_0^2 \ c_1 \ d_1 \ c_2 \ d_2 \ \ldots \ c_K \ d_K]^T$$

$$\epsilon = [\epsilon_P(t_1^1) \ \epsilon_P(t_2^1) \ \ldots \ \epsilon_P(t_N^1) | \ \ldots \ | \epsilon_P(t_1^M) \ \epsilon_P(t_2^M) \ \ldots \ \epsilon_P(t_N^M)]^T$$

$$X = \begin{bmatrix} 1 & 0 & \cos(2\pi f_1 t_1^1) & \sin(2\pi f_1 t_1^1) & \cos(2\pi f_2 t_1^1) & \sin(2\pi f_2 t_1^1) & \cdots & \cos(2\pi f_K t_1^1) & \sin(2\pi f_K t_1^1) \\ 1 & 0 & \cos(2\pi f_1 t_2^1) & \sin(2\pi f_1 t_2^1) & \cos(2\pi f_2 t_2^1) & \sin(2\pi f_2 t_2^1) & \cdots & \cos(2\pi f_K t_2^1) & \sin(2\pi f_K t_2^1) \\ \vdots & \vdots & \vdots & \vdots & \vdots & \vdots & & \vdots & \vdots \\ 1 & 0 & \cos(2\pi f_1 t_N^1) & \sin(2\pi f_1 t_N^1) & \cos(2\pi f_2 t_N^1) & \sin(2\pi f_2 t_N^1) & \cdots & \cos(2\pi f_K t_N^1) & \sin(2\pi f_K t_N^1) \\ \vdots & \vdots & \vdots & \vdots & \vdots & \vdots & & \vdots & \vdots \\ 1 & \overline{0} & \overline{\cos(2\pi f_1 t_1^M)} & \overline{\sin(2\pi f_1 t_1^M)} & \overline{\cos(2\pi f_2 t_1^M)} & \overline{\sin(2\pi f_2 t_1^M)} & \cdots & \overline{\cos(2\pi f_K t_1^M)} & \overline{\sin(2\pi f_K t_1^M)} \\ 1 & 0 & \cos(2\pi f_1 t_2^M) & \sin(2\pi f_1 t_2^M) & \cos(2\pi f_2 t_2^M) & \sin(2\pi f_2 t_2^M) & \cdots & \cos(2\pi f_K t_2^M) & \sin(2\pi f_K t_2^M) \\ \vdots & \vdots & \vdots & \vdots & \vdots & \vdots & & \vdots & \vdots \\ 1 & 0 & \cos(2\pi f_1 t_N^M) & \sin(2\pi f_1 t_N^M) & \cos(2\pi f_2 t_N^M) & \sin(2\pi f_2 t_N^M) & \cdots & \cos(2\pi f_K t_N^M) & \sin(2\pi f_K t_N^M) \end{bmatrix} \quad (8)$$

The goal is to estimate the parameter vector $\Theta$ for the inspiratory flow and pressure segments from which $Z^{insp}$ can be calculated according to Equation 3. To accomplish this, a weighted least squares (WLS) estimate of $\Theta$, denoted as $\hat{\Theta}$, can be computed as:

$$\hat{\Theta} = (X^T W X)^{-1} X^T W Y \quad (9)$$

where W is the MN×NM diagonal weighting matrix, whose elements contain the squares of the weighting function $w(t_n^m)$. The purpose of the weighting function $w(t_n^m)$ is to minimize the estimation bias of $\hat{\Theta}$ due to the deterministic components of $\epsilon$. Since these deterministic components will vary depending on the patient's pathophysiology or the instrumentation used, the choice of weighting function to use is arbitrary. The impact of various weighting techniques is explored below.

The following sections highlight the results of simulation and experimentation carried out by the inventors. The data are provided by way of example only, and the computational techniques are given as preferred embodiments for carrying out the present invention. Other techniques and embodiments are equally applicable to the principles of the present invention.

Simulation Studies

Figure 3A:
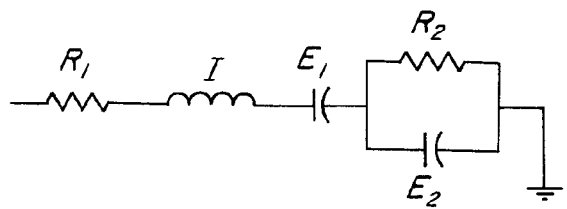
FIGS. 3A and 3B are schematic diagrams of electrical analogues of lumped-element models used to simulate mechanical ventilation data for healthy and diseased lungs respectively.
Figure 3B:
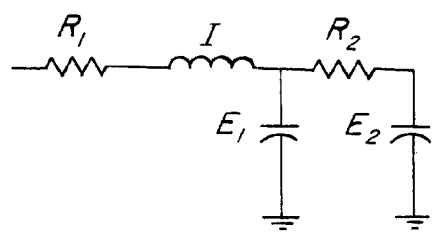

Inspiratory flow and pressure data was simulated from two different linear lumped element models. Both models can mimic the transient and steady-state mechanical behavior of lungs and/or total respiratory system during mechanical ventilation. Model 1 (FIG. 3A) is often used to describe the mechanics of healthy lungs, since it assumes that both transient and steady state dynamics arise solely from the viscoelastic properties of the tissues. Here a Newtonian resistance $R_1$, airway inertance I, and static elastance element $E_1$ are in series with the viscoelastic parallel resistance-elastance combination $R_2$-$E_2$. For the lungs alone, $R_1$ would represent airway resistance, while for the total respiratory system, $R_1$ would represent both airway resistance and any purely Newtonian component of the chest wall resistance. For model 2 (FIG. 3B), a central airway component $R_1$-I is separated from a peripheral resistance $R_2$ by an airway wall elastance element $E_1$, and there is a single tissue elastance $E_2$. This model was originally proposed by Mead (see Mead, J., "Contribution of compliance of airways to frequency-dependent behavior of lungs", *J. Appl. Physiol.* 26: 670–673, 1969), and assumes that the dominant mechanism contributing to frequency dependence of R and E is the shunting of flow into the airway walls in the presence of increased peripheral impedance. Even though these two models differ topologically in the proposed mechanism for frequency dependence of R and E, both admit the same form of pressure-flow Laplace transfer function:

$$Z(s) = \frac{P(s)}{\dot{V}(s)} = \frac{B_3 s^3 + B_2 s^2 + B_1 s + B_0}{s(s + A_1)} \quad (10)$$

which becomes an analytical expression for the impedance of the model when $s = j2\pi f_k$. The values of the coefficients $B_3$, $B_2$, $B_1$, $B_0$, and $A_1$ will depend on the particular model topology used. For either of the models shown in FIG. 3, the differential equation describing the inspiratory pressure dynamics is the form:

$$\dot{P}(t) + A_1 P(t) = B_3 \dddot{V}(t) + B_2 \ddot{V}(t) + B_1 \dot{V}(t) + B_0 V(t) \quad (11)$$

where for model 1:

$$B_3 = I, \quad B_2 = R_1 + \frac{IE_2}{R_2}, \quad B_1 = \frac{R_1 E_2}{R_2} + E_1 + E_2, \quad B_0 = \frac{E_1 E_2}{R_2}, \text{ and}$$

$$A_1 = \frac{E_2}{R_2}$$

and for model 2:

$$B_3 = I, \quad B_2 = R_1 + \frac{I}{R_2}(E_1 + E_2), \quad B_1 = \frac{R_1 E_1 + R_1 E_2 + R_2 E_1}{R_2},$$

$$B_0 = \frac{E_1 E_2}{R_2}, \text{ and } A_1 = \frac{E_1 + E_2}{R_2}$$

Parameter values for both models shown below in Table 2 were selected to simulate the inspiratory dynamics of healthy (model 1) and severely obstructed (model 2) lungs in the absence of flow limitation, as derived from D'Angelo et al. (see D'Angelo, E., F. M. Robatto, E. Calderini, M. Tavola, D. Bono, G. Torri, and J. Milic-Emili, "Pulmonary and chest wall mechanics in anesthetized paralyzed humans", *J. Appl. Physiol.* 70: 2602–2610, 1991) and Mead (see Mead, J., "Contribution of compliance of airways to frequency-dependent behavior of lungs", *J. Appl. Physiol.* 26: 670–673, 1969):

TABLE 2

| Model | $R_1$ | I | $E_1$ | $R_2$ | $E_2$ |
|---|---|---|---|---|---|
| 1 | 1.85 | 0.01 | 8.2 | 3.44 | 3.21 |
| 2 | 1.50 | 0.01 | 200.0 | 7.50 | 2.50 |

Units: $R_1$, $R_2$ - cm $H_2O$/L/s; $E_1$, $E_2$, - cm $H_2O$/L; I - cm $H_2O$/L/$s^2$ To make these simulations as close as possible to the experimental conditions described below, the following approach was taken. The two inspiratory flow segments of the EVW were digitally generated with a sampling rate of 640 Hz. The corresponding pressure response to each flow segment was computed according to Equation 11 using an Euler predictor-corrector technique, as described in Kincaid, D., and W. Cheney, *Numerical Analysis: Mathematics of Scientific Computing,* Pacific Grove, Calif.: Brooks/Cole Publishing Company, 1991, with all state variables set to zero at the start of each inspiration. Thus, each inspiratory pressure segment contained both transient and steady-state components. All inspiratory flow and pressure segments were separately passed through a 4-pole digital Butterworth low pass filter with a cutoff frequency of 10 Hz, and then re-sampled at 40 Hz. The trigonometric coefficients of Equations 1 and 2 were then estimated from four of these resampled flow and pressure inspirations according to Equation 7, and $Z^{insp}$ was computed according to Equation 9. This $Z^{insp}$ was compared to the true impedance Z as computed according to Equation 10.

Impact of Pressure Transient Duration

For the system of Equation 11, the pressure transient response will be a single exponential with a time constant given by $\tau = 1/A_1$, which for model 1 is:

$$\tau = \frac{R_2}{E_2} \quad (12)$$

and for model 2 is:

$$\tau = \frac{R_2}{E_1 + E_2} \quad (13)$$

To investigate the effects of the duration of these pressure transients on the estimated $Z^{insp}$, flow and pressure data were simulated from model 1 with $R_1$, $E_1$, and $E_2$ given by Table 2 but with $R_2$ varied from 0.1027 to 10.27 cm $H_2O/L/s$, yielding values of $\tau$ from 0.032 to 3.2 seconds, corresponding to duration lengths of 1 to 100% of $T_1$.

Impact of Noise

The impact of random noise on the estimates of $Z^{insp}$ was evaluated by adding zero-mean, white Gaussian noise to both the flow and pressure inspirations just prior to filtering and decimation. Noise variances were adjusted to 1, 5, and 10% of the inspiratory flow or pressure variances, corresponding to signal-to-noise ratios (SNR's) of 20, 13, and 10 dB, respectively. To avoid correlated noise between flow and pressure, the noise added to the flow was not allowed to propagate through the system of Equation 11.

Impact of Harmonic Distortion

As with the OVW, the frequencies of the EVW follow an NSND pattern to minimize the effects of harmonic distortion during broad-band excitation at these frequencies. This aspect of the signal was motivated by the finding that parenchymal and chest wall resistance and elastance decrease as tidal volume increases, as explained in Suki, B. "Nonlinear phenomena in respiratory mechanical measurements", *J. Appl. Physiol.* 74: 2574–2584, 1993. With an NSND design, one can estimate the apparent linear Z at the tidal volume delivered, as explained in Suki, B., and K. R. Lutchen, "Pseudorandom signals to estimate apparent transfer and coherence functions of nonlinear systems: applications to respiratory mechanics", *IEEE Trans. Biomed. Eng.* 39: 1142–1151, 1992. Thus to evaluate the impact of nonlinear harmonic distortion on the WLS analysis, pressure inspirations were simulated from a simple Wiener model (see Suki, B., Q. Zhang, and K. R. Lutchen, "Relationship between frequency and amplitude dependence in the lung: a nonlinear block-structured modeling approach", *J. Appl. Physiol.* 79: 660–671, 1995) in which a static nonlinear subsystem distorts the linear P(t) from Equation 11. The nonlinear subsystem was chosen as:

$$P_{nl}(t) = a_1 P(t) + a_2 P^2(t) + a_3 P^3(t) \quad (14)$$

which has been shown to mimic the inverse tidal volume dependence of tissue resistance and elastance. Note that Equation 14 does not account for dynamic airway compression and flow limitation, which are much stronger nonlinear processes and are avoided by the inspiratory-only analysis.

For these simulations, four EVW inspiratory flow segments appropriately scaled to 250, 500, and 750 ml inspiratory tidal volumes were separately passed through the linear subsystem of Equation 11 to yield corresponding linear inspiratory pressure segments. Each pressure segment P(t) was then passed through the static nonlinear system of Equation 14, with $a_1 = 1$, $a_2 = -0.037$ cm$H_2O^{-1}$, and $a_3 = 0.0011$ cm$H_2O^{-2}$(36) to give the final output $P_{nl}(t)$ which was then substituted for P(t) in the Y vector of Equation 8 to estimate $Z^{insp}$.

Data Analysis and Accuracy of $Z^{insp}$ Estimates

Various weighting functions for the WLS analysis were evaluated in their ability to estimate the true Z from the inspiratory flow and pressure data. A primary concern was to minimize the bias due to physiological and instrumentation transients, both of which decay with time. Thus, weighting functions were selected that de-emphasized data at the beginning of an inspiration. These included a rising exponential function which reaches unity by the middle of $T_1$:

$$w(t_n^m) = 1 - \exp(-10(t_n^m - t_1^m)/T_1), \; t_1^m \leq t_n^m \leq t_N^m \quad (15)$$

as well as one whose first half consists of the rising portion of a Hanning window of length $T_1$:

$$w(t_n^m) = \begin{cases} \frac{1}{2}\left[1 - \cos\left(\frac{2\pi(t_n^m - t_1^m)}{T_1}\right)\right], & t_1^m \leq t_n^m < t_1^m + \frac{T_1}{2} \\ 1, & t_1^m + \frac{T_1}{2} \leq t_n^m \leq t_N^m \end{cases} \quad (16)$$

Other weighting functions are equally applicable to the present invention. With an experimental system capable of generating EVWs, additional disturbances or artifacts may be at the beginning and end of the inspiratory waveforms due to the finite opening and closing time of valves directing flow to and from the patient. In this situation, it may be desirable to give the most weight to the data at the middle of the inspiration. Thus, $Z^{insp}$ was also estimated with each inspiration weighted by a full Hanning window. The above weighting schemes were compared to the case with no weighting (i.e., W=I in Equation 9, where I is the identity matrix). This represents the ordinary least squares solution of $\Theta$, with $\hat{\Theta}(X^T X)^{-1} X^T Y$ and all errors equally weighted (26). In this case, the bias in $\hat{\Theta}$ due to deterministic errors will be maximum.

The accuracy of each estimated $Z^{insp}$ was assessed according to its percent distance $D_Z$ from the true Z at each $f_k$:

$$D_Z(f_k) = \frac{|Z(f_k) - Z^{insp}(f_k)|}{|Z(f_k)|} \times 100\% \quad (17)$$

Comparisons among different weighting schemes were made using $D_Z$ averaged over all $f_k$'s:

$$\overline{D}_Z = \frac{1}{K}\sum_{k=1}^{K}[D_Z(f_k)] \quad (18)$$

Experimental System

Figure 4:
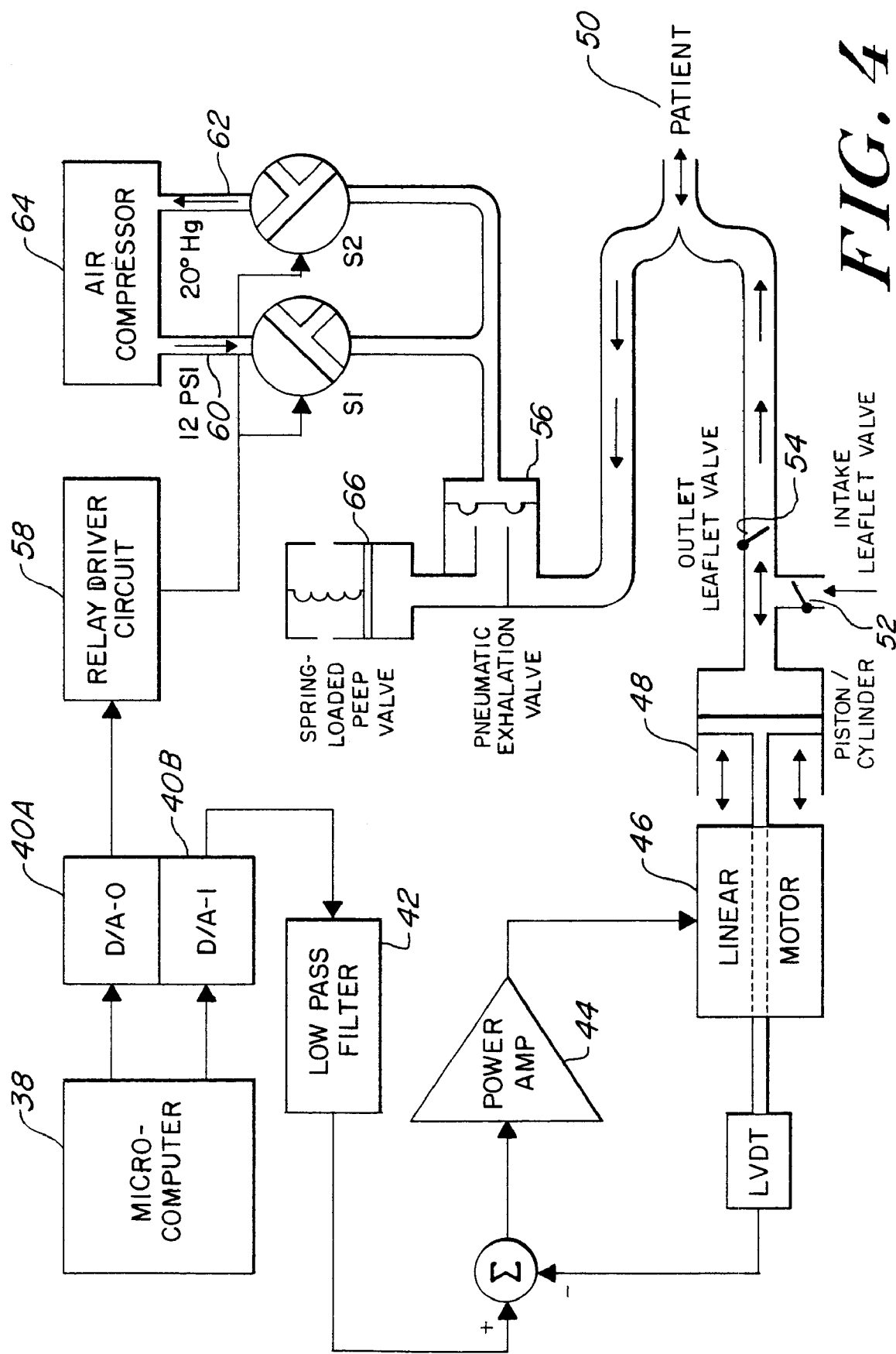
FIG. 4 is a schematic block diagram of a preferred embodiment of a ventilator system used to deliver EVW to patients in accordance with the present invention.

A preferred embodiment of an apparatus for delivering EVWs to patients is schematized in FIG. 4. The desired inspiratory flow pattern is generated from one channel of a D/A converter 40B (for example, D/A-1, Data Translations DT-2811) at a rate of 40 Hz, low pass filtered by filter 42 at 10 Hz (for example, Frequency Devices), and presented to a servo-amplifier 44 which drives a linear motor 46 (for example, Infomag) connected to a piston-cylinder arrangement 48. Precise control of flows to and from the patient 50 is obtained using two unidirectional leaflet valves 52, 54 (for example, DeVilbiss 2-1019) and a pneumatically-controlled exhalation valve 56 (for example, Nellcor Puritan Bennett Part No. 4-020710-00). During inspiration, the net forward motion of the piston 48 generated sufficient positive pressure in the cylinder to open the outlet leaflet valve 54 and keep the intake leaflet valve 52 closed. Precisely at end inspiration (when the piston has reached its maximal forward displacement), the exhalation valve 56 is triggered opened by an additional D/A channel 40A (for example, D/A-0). The diaphragm position of this exhalation valve 56 is controlled pneumatically. Thus, the additional D/A channel 40A toggles two 3-way solenoid valves S1, S2, (for example, Predyne, New Britain, Conn.) via a relay driver circuit 58 to control the presentation of either 12 PSI compressed air 60 or 20" Hg suction 62 to the valve 56 from a 1/45 HP compressor 64 (for example, Air Cadet 7530-40, Cole-Palmer Instrument Co.). The back-pressure generated by the passive exhalation of the patient closes the outlet leaflet valve 54, while the simultaneous backstroke of the piston 56 generates sufficient negative pressure to open the intake leaflet 52 and bring fresh gas from the atmosphere into the cylinder. PEEP is provided by spring-loaded valve 66 connected to the outlet of the exhalation valve 56.

The embodiment of FIG. 4 was employed in an experiment, the results of which are given below.

Experimental Measurements

EVW measurements, shown in Table 3 (below) were made in four anesthetized, paralyzed, and intubated adult patients undergoing elective thoracic surgery. The protocol was approved by institutional research committees, and informed consent was obtained from each patient. Two of the patients (1 and 2) demonstrated mild obstruction on pulmonary function testing several weeks prior to surgery. The other two (3 and 4) exhibited severe obstruction with flow-volume loops consistent with expiratory flow limitation during normal breathing maneuvers.

TABLE 3

Physical data for thoracic surgery patients

| Subject | Age (yrs) | Gender | FEV$_1$ (% predicted) | FEV$_1$/FVC (%) | Diagnosis | Surgical Procedure |
|---|---|---|---|---|---|---|
| 1 | 27 | F | 81 | 90 | Metastatic Osteo-sarcoma | Thoraco-scopic biopsy |

TABLE 3-continued

Physical data for thoracic surgery patients

| Subject | Age (yrs) | Gender | FEV$_1$ (% predicted) | FEV$_1$/FVC (%) | Diagnosis | Surgical Procedure |
|---|---|---|---|---|---|---|
| 2 | 69 | M | 79 | 77 | non-small cell carcinoma | Thoraco-scopic resection |
| 3 | 47 | F | 31 | 28 | COPD | lung volume reduction |
| 4 | 66 | M | 14 | 25 | COPD | lung volume reduction |

FEV$_1$: Forced expiratory volume in 1 second
FVC: Forced vital capacity
COPD: Chronic obstructive pulmonary disease After induction of anesthesia/paralysis, each patient was intubated with a single-lumen endotracheal tube and maintained on volume-cycled ventilation. Esophageal pressure was obtained with a balloon catheter inserted orally, the distal tip of which was positioned 35–40 cm from the incisors. Flow was measured with a pneumotach (for example, Hans Rudolph 4700A) placed at the proximal end of the endotracheal tube and connected to a 0–2 cm $H_2O$ variable reluctance pressure transducer (for example, Celesco LCVR-0002). Tracheal pressure was obtained with a small polyethylene catheter placed into the endotracheal tube and allowed to extend approximately 2 cm beyond its distal end. Changes in transpulmonary pressure were then estimated as the difference between tracheal and esophageal pressures across a single 0–50 cm $H_2O$ variable reluctance pressure transducer (for example, Celesco LCVR-0050).

Each patient received between six to seven 500 ml EVW breaths. To reduce the impact of alveolar recruitment on the pressure waveforms, all measurements were made at 3 cm $H_2O$ PEEP. Each run lasted approximately 40–50 seconds, during which time arterial oxygen saturation, systemic arterial pressure, central venous pressure, and EKG were continuously monitored by the attending anesthesiologist. The two patients with mild obstruction showed no evidence of expiratory flow limitation. Thus the traditional OVW of FIG. 2A was also applied in these patients and compared to the EVW results. For OVW data, the "true" lung impedance ($Z_L$) was computed using a standard power spectral approach with rectangular windowing.

Simulation Studies

Figure 5A:
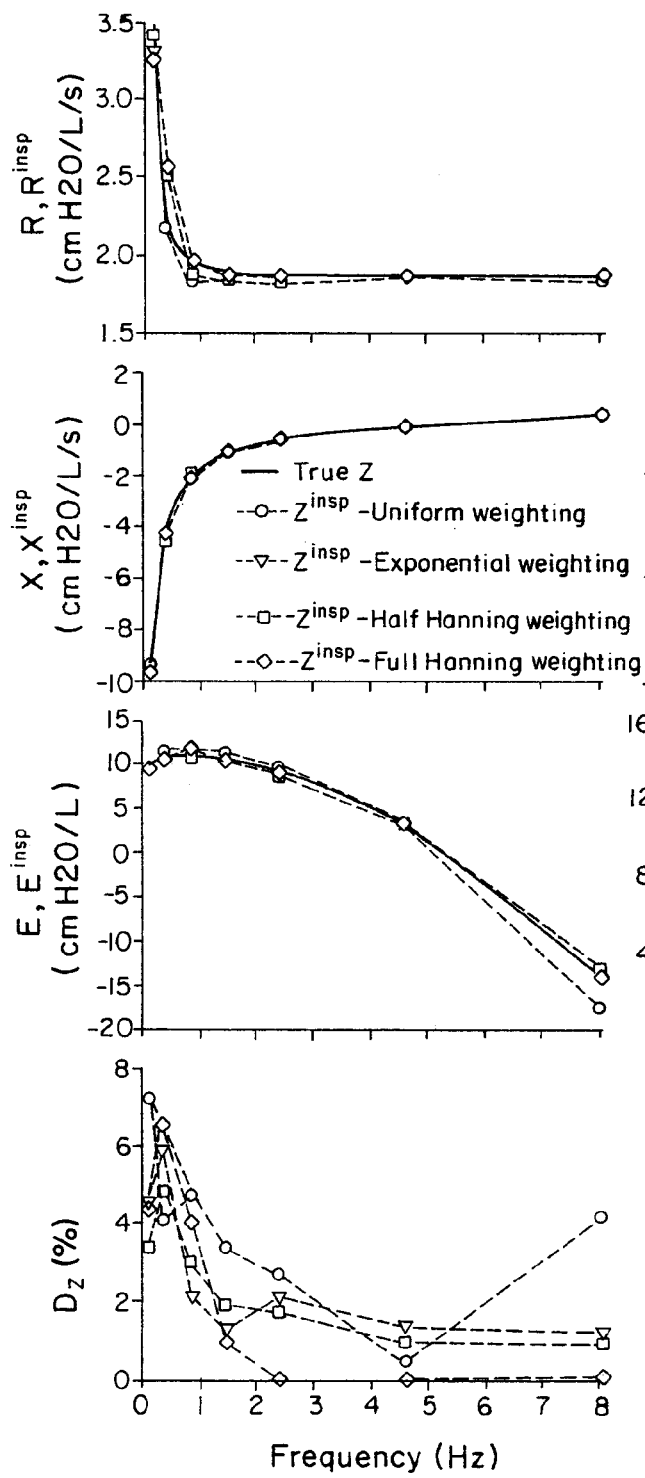
FIGS. 5A and 5B are charts for comparing WLS estimates of $R^{insp}$, $X^{insp}$, and $E^{insp}$ spectra from simulated EVW inspiratory segments with different weighting techniques: uniform (○), exponential (▽), half Hanning (□), and full Hanning (◇) for the first and second models of FIG. 3.
Figure 5B:
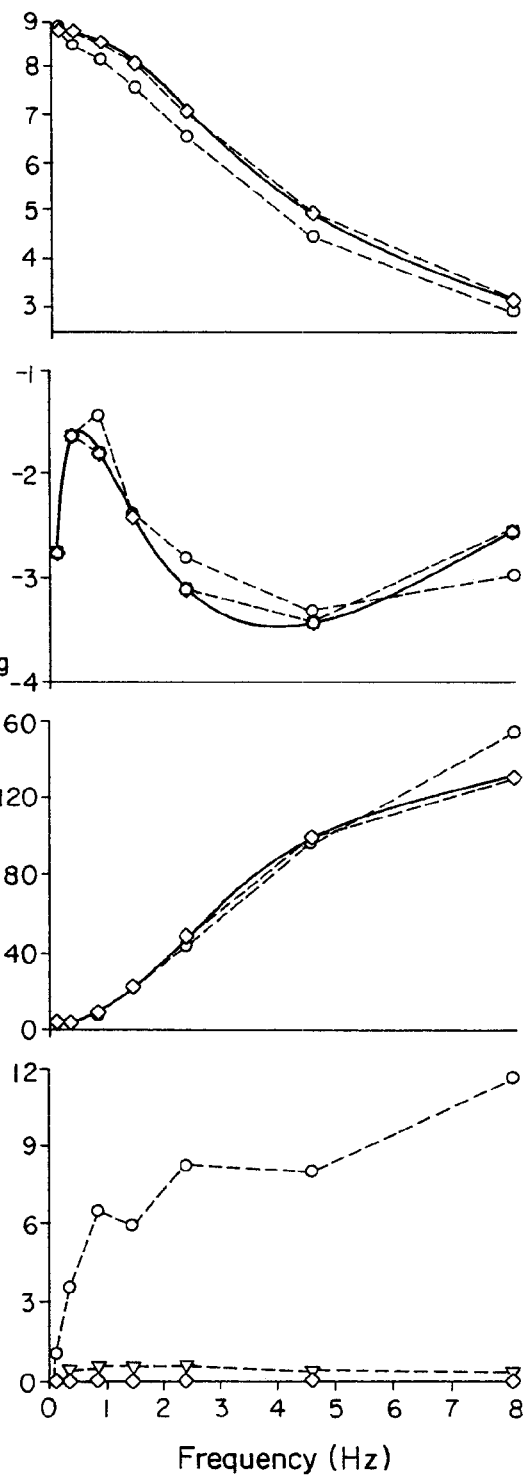

FIGS. 5A and 5B compare the true Z and estimated $Z^{insp}$ computed from the simulated EVWs for model 1 and model 2 respectively. Shown are the resistive (R) and reactive (X) components of the impedances, as well as the effective elastance ($E=-2\pi f_k X$). Note that the frequency dependent features of the true Z for models 1 and 2 are quite different, despite being described by the same form of transfer function (Equation 10). This is due to the different parameter values assigned to each of the models to reflect different physiological processes. The $D_Z$ at each $f_k$ for the various weighting schemes are also shown, while the corresponding $\overline{D}_Z$ for each weighting scheme is shown in Table 4, which summarizes the impact of different weighting schemes on percent distance between the true Z and estimated $Z^{insp}$ averaged over all frequencies:

TABLE 4

| Weighting | Model 1 | Model 2 |
|---|---|---|
| Uniform | 3.78 | 6.39 |
| Exponential | 2.64 | 0.42 |
| Half Hanning | 2.41 | 0.01 |
| Full Hanning | 2.27 | 0.01 |

For model 1 (representing a healthy lung), all $Z^{insp}$ estimates match the true Z well and showed only minor deviations regardless of the weighting scheme used, with the greatest $D_Z$ noted for frequencies below 1 Hz. For uniform weighting, $D_Z$ ranged from 0.4 to 7.2%, with $\overline{D}_Z$=3.78%. All other weighting schemes resulted in slightly lower $\overline{D}_Z$ values, with the lowest being obtained for full Hanning weighting.

In contrast, $R^{insp}$ for model 2 estimated with uniform weighting was systematically lower than the true R at all frequencies, while the respective $X^{insp}$ showed considerable scatter. The $D_Z$ for uniform weighting ranged from 1.0 to 11.6% with $\overline{D}_Z$=6.39%, while other weighting schemes yielded substantially lower $D_Z$ values at all frequencies. The $\overline{D}_Z$ obtained for both the half and full Hanning weighting schemes were practically negligible.

Table 5 shows the impact of increasing pressure transient duration $\tau$ on $\overline{D}_Z$ on the percent distance between the true Z and estimated $Z_{insp}$ averaged over all frequencies for all weighting schemes.

TABLE 5

| Pressure Transient Duration (% of $T_1$) | Uniform Weighting | Exponential Weighting | Half Hanning Weighting | Full Hanning Weighting |
|---|---|---|---|---|
| 1 | 5.82 | 0.03 | 0.02 | 0.02 |
| 5 | 4.58 | 0.34 | 0.04 | 0.12 |
| 10 | 3.66 | 0.77 | 0.33 | 0.63 |
| 15 | 3.34 | 1.23 | 0.89 | 1.21 |
| 25 | 3.47 | 2.18 | 1.90 | 1.98 |
| 50 | 4.37 | 2.91 | 2.77 | 2.37 |
| 75 | 4.99 | 2.76 | 2.69 | 2.15 |
| 100 | 5.39 | 2.48 | 2.44 | 1.89 |

For the exponential and Hanning weighting schemes, there was a trend of increasing $\overline{D}_Z$ with increasing $\tau$ up to 50% of $T_1$, but thereafter remained fairly constant. At every $\tau$, uniform weighting resulted in the highest $\overline{D}_Z$. Also for any given $\tau$, both the full and half Hanning weighting schemes resulted in a lower $\overline{D}_Z$ compared to exponential weighting. While both Hanning weighting schemes performed similarly with the simulated data, it should be pointed out that full Hanning weighting has the additional advantage of tapering the end of the inspiration to zero. This may be desirable under experimental conditions when valve switching introduces additional disturbances at the end of inspiration. For this reason, the embodiment described hereinafter assumes WLS with full Hanning weighting.

The impact of noise level on flow and pressure on the $Z^{insp}$ estimates are given in Table 6, which assumes WLS with full Hanning weighting for models 1 and 2.

TABLE 6

| SNR (dB) | Model 1 | Model 2 |
|---|---|---|
| ∞ | 2.27 | 0.15 |
| 20 | 4.28 | 0.53 |
| 13 | 7.61 | 1.49 |
| 10 | 11.61 | 2.02 |

For both models, $\overline{D}_Z$ increased as SNR decreased. Nevertheless, $\overline{D}_Z \leq 11.61\%$ and 2.02% for model 1 and model 2 respectively, even at SNRW=10 dB. At all noise levels, values of $\overline{D}_Z$ for model 2 were substantially lower than those for model 1.

The effects of the simple polynomial nonlinearity of Equation 14 on the estimated $Z^{insp}$ for both models 1 and 2 are shown in FIGS. 6A and 6B, which are charts for comparison of $R^{insp}$, $X^{insp}$, and $E^{insp}$ spectra estimated from EVW data at tidal volumes of 250 (●), 500 (○), and 750 (◆) ml. Inspiratory pressure data was simulated with a simple Wiener model with linear subsystem given by Equation 11 and nonlinear subsystem given by Equation 14. Also shown are the true R, X, and E spectra from the linear subsystem of Equation 10 (solid lines). Since this type of nonlinearity is expected to demonstrate inverse tidal volume dependence in tissue resistance and elastance, the $D_Z$ between the true Z of the linear subsystem and the estimated $Z^{insp}$ for the entire system are not shown. Note that in the presence of both transients and harmonic distortion, the spectral estimates of $Z^{insp}$ are smooth and follow the frequency dependent features of Z for the linear subsystem of either model. Consistent with this type of nonlinear model, both $R^{insp}$ and $E^{insp}$ decrease with increasing tidal volume. Thus even with nonlinearities expected in the respiratory tissues, the EVW provides an accurate and smooth estimate of $Z^{insp}$ for the tidal volume delivered.

Experimental Data

Figures 7A, 7B:
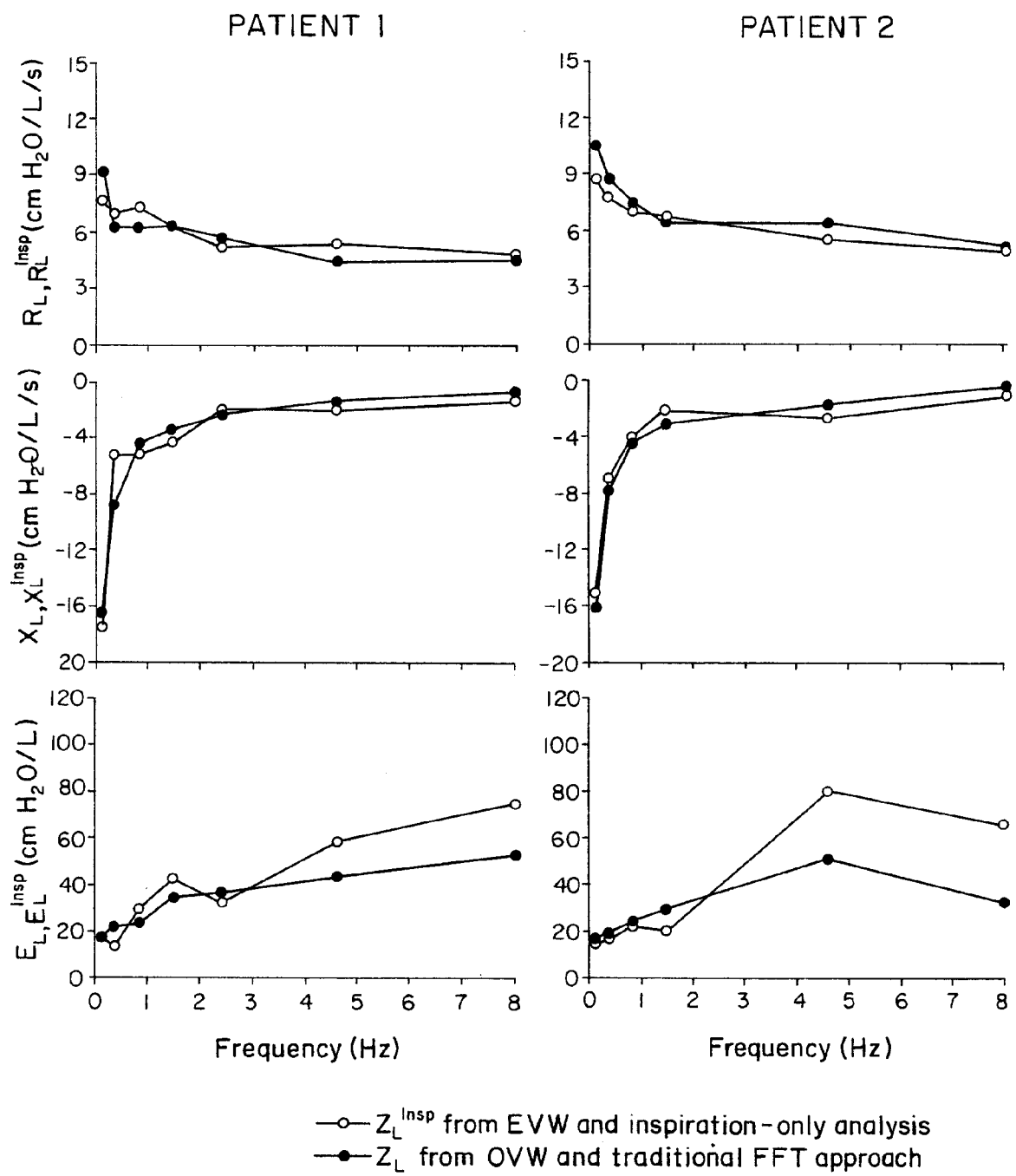
FIGS. 7A and 7B are charts for comparison of lung resistance, reactance, and elastance estimated for first and second anesthetized, paralyzed, and intubated patients with mild obstruction respectively, using the weighted-least-squares (WLS) approach on four EVW inspiratory segments (○) and a traditional power spectral approach with four full OVW breaths (●), in accordance with the present invention.

FIGS. 7A and 7B compare lung impedance estimates for the two patients (see Table 3) with mild obstruction using: 1) the WLS inspiratory-only analysis of the EVW; and 2) the traditional FFT-approach on a standard OVW. For Patient JK, data at 2.42 Hz was omitted from the figure due to corruption by cardiac artifact. The estimated $R_L^{insp}$ and $X_L^{insp}$ are in close agreement with the $R_L$ and $X_L$ obtained from the traditional spectral approach on the OVW. The average $D_Z$ between the two approaches was 16.33+/−11.43% for Patient 1, and 12.69+/−4.25% for Patient 2. Although $X_L$ and $_L^{insp}$ were in close agreement at all $f_k$s, some discrepancies were noted between $E_L$ and $E_L^{insp}$ above 3 Hz.

Figures 8A, 8B:
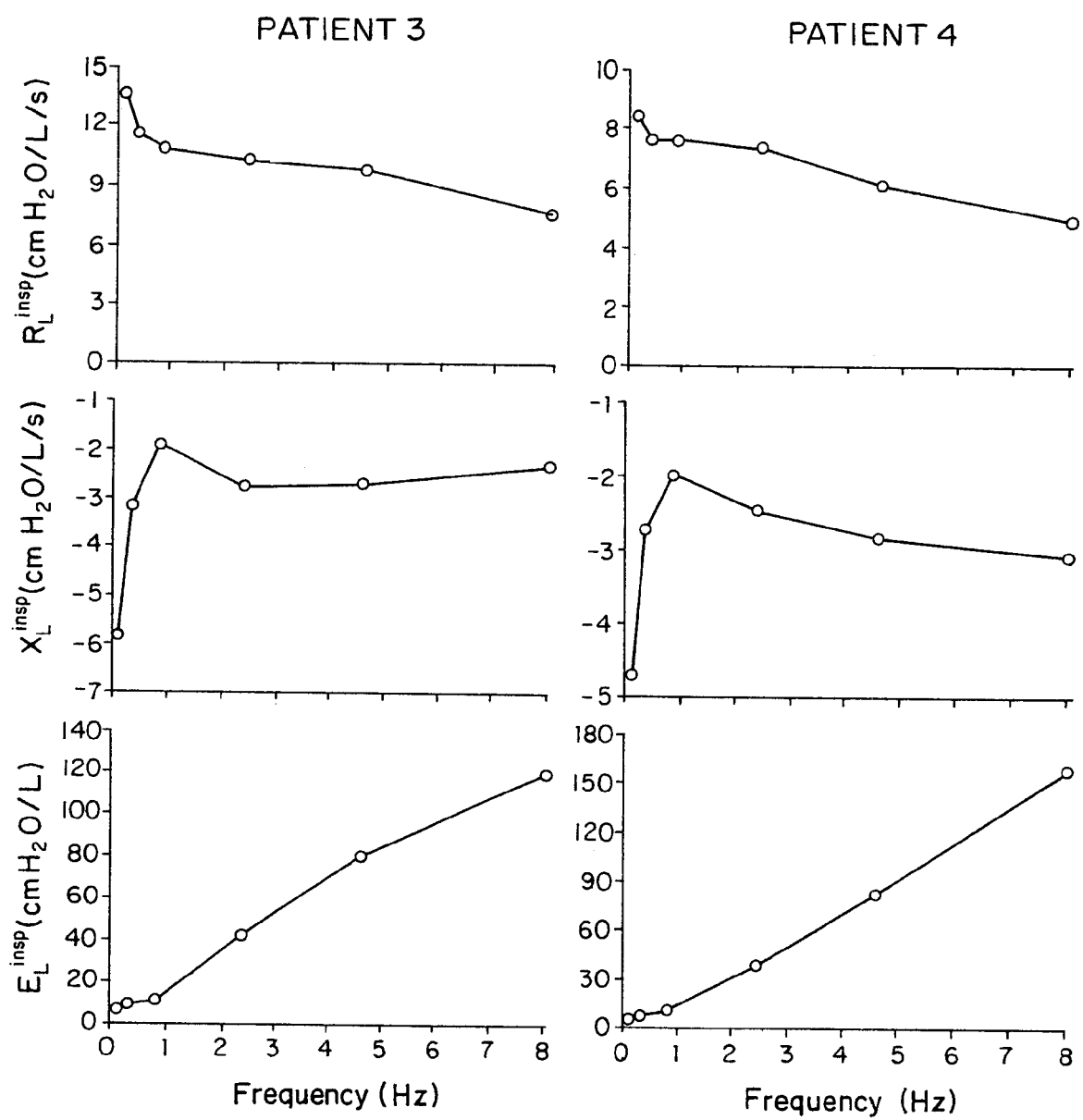
FIGS. 8A and 8B are charts of inspiratory lung resistance, reactance, and elastance spectra in two anesthetized, paralyzed, and intubated patients with COPD estimated from the WLS on four EVW inspiratory segments, in accordance with the present invention.

The WLS estimates of $Z_L^{insp}$ for the two patients with severe emphysema are shown in FIGS. 8A and 8B. Both patients demonstrated a pronounced positive frequency dependence in $E_L^{insp}$, suggesting the presence of severe peripheral airway obstruction. Interestingly, the $R^{insp}$ of both COPD patients were only slightly elevated from those of the moderately obstructed patients in FIG. 7, despite drastic differences in $FEV_1$ (see Table 3). Thus, it may be reasonable to attribute much of the low $FEV_1$ in the COPD patients to reduced elastic recoil and/or premature airway collapse rather than bronchitic airway disease. Both COPD patients demonstrated lower $E_L^{insp}$ values at 0.15625 Hz compared to the mildly obstructed patients (5.74 and 4.62 cm $H_2O$/L vs. 17.06 and 14.84 cm $H_2O$/L), consistent with emphysematous lungs.

Discussion

It has been established theoretically and experimentally that total respiratory or pulmonary impedance measured over breathing rates from 0.1 to 10 Hz is a sensitive indicator of lung disease, particularly peripheral airway obstruction. Despite many recent advances in instrumentation, signal processing, and modeling analyses, the measurement of Z over this bandwidth remains difficult in ventilator-dependent patients with compromised pulmonary function, since conventional forced oscillation techniques can jeopardize their safety. Moreover, since Z is really a construct to describe linear and time-invariant systems, its measurement by such conventional techniques is difficult to interpret in the presence of highly nonlinear processes such as dynamic airway compression and flow limitation.

Since the 1950's, physiologists have recognized that linear approximations of respiratory mechanics in patients with COPD must be restricted to inspiratory maneuvers if they are to be valid. In keeping with this line of reasoning, the $Z^{insp}$ construct of the present invention provides an alternative technique to characterize respiratory mechanics in such patients. While $Z^{insp}$ does not necessarily provide a quantitative index of dynamic airway compression and flow-limitation (which are often the major contributing factors to compromised lung function in COPD patients), it nonetheless provides unique insight into the level and distribution of obstruction to inspiratory flows. By ensuring the maintenance of clinically appropriate ventilation during periods of oscillatory flow excitation, the EVW and WLS analysis provides an accurate and valid estimate of $Z^{insp}$ in an otherwise inaccessible group of patients.

Computational Considerations

A linear least squares approach to estimate $Z^{insp}$ may seem unorthodox in this situation, since not all of the stringent steady-state requirements implicit in an impedance computation are met. A necessary assumption of this approach is that the magnitude of the transient responses (or any deterministic components of $\epsilon$ in Equation 6) are sufficiently small enough such that both flow and pressure will be dominated by their respective linear steady-state oscillations over the inspiratory period. Given the model of Equation 6, this would require that:

$$\|\epsilon\| << \|X\Theta\|$$

where $\|.\|$ denotes the Euclidean norm of the enclosed vector. In the present case, this assumption is indeed valid, as simulations demonstrate that even long-duration transients (Table 5) and harmonic distortions (FIG. 6) typical of those associated with mechanical ventilation will have minimal impact on an inspiration-based estimate of Z.

Figure 9A:
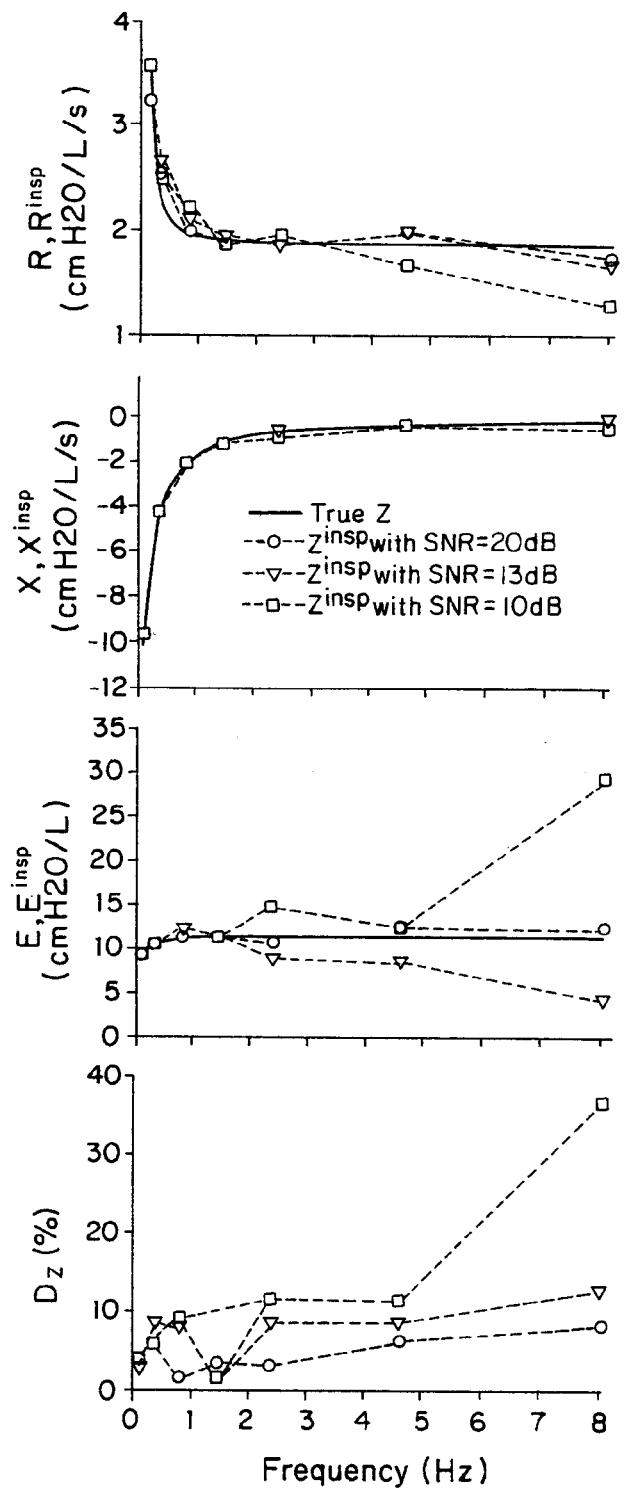
FIGS. 9A and 9B are charts for comparisons of $R^{insp}$, $V^{insp}$, and $E^{insp}$ spectra estimated from EVW flow and pressure data at signal-to-noise ratios of 20 (○), 13 (▽), and 10 (□) dB for the first and second models respectively, in accordance with the present invention.
Figure 9B:
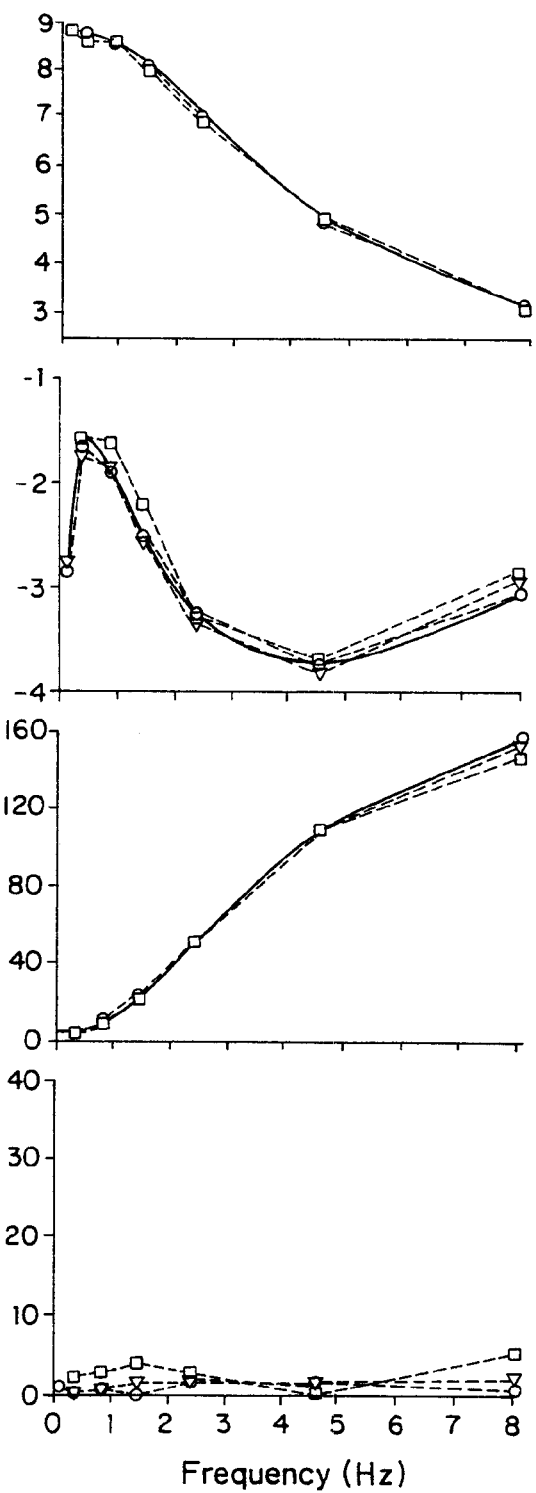

Despite the close agreement between the true Z and WLS-estimated $Z^{insp}$ of the simulation studies, some discrepancies between the OVW-based EL estimate and the EVW-based $E_L^{insp}$ estimates were observed in the two mildly-obstructed patients above 3 Hz. Much of this discrepancy may reflect the low signal-to-noise ratio of the reactive (out-of-phase) component of the pressure at high frequencies. In healthy awake subjects, nearly all of the reactive pressure from 3–8 Hz results from the inertia of gas in the central airways. However, much of this inertial pressure drop is avoided in intubated subjects when tracheal pressure is measured at the distal end of the endotracheal tube. Both $X_L$ and $X_L^{insp}$ will approach zero with increasing frequency, as Subjects BD and JK demonstrate (see FIGS. 7A and 7B). Thus in healthy subjects, both $E_L$ and $E_L^{insp}$ would be less reliable at higher frequencies due to noise sensitivity, since $E_L = -2\pi f X_L$. However in patients with severe peripheral airway obstruction, much of the high frequency reactive pressure can reflect the distensibility of more proximal airways. In COPD patients, $X_L^{insp}$ will not approach zero until much higher frequencies, thus making their $E_L^{insp}$ more reliable over the 3–8 Hz range. Although an OVW-based $X_L$ in the COPD patients could not be measured to verify this hypothesis, EVW flow and pressure data were simulated with different noise levels using the healthy and diseased models of FIG. 3, but with I=0 in each to mimic the effects of tracheal intubation on $Z^{insp}$. FIGS. 9A and 9B compare the true Z and estimated $Z^{insp}$ for both models 1 and 2 with uncorrelated white Gaussian noise on the flow and pressure at SNRs of 20, 13, and 10 dB, along with corresponding $D_z$s. Consistent with predictions, the $D_Z$ between $Z^{insp}$ and the true Z increases with both frequency and noise level for the model 1 simulations, but only small discrepancies are observed for the model 2 simulations at any noise level. Thus, while estimates of $E_L^{insp}$ at high frequencies may be unreliable in intubated healthy subjects, they are probably more accurate in COPD patients due to the effects of airway wall shunting on $X_L$.

An additional concern arises when one considers that the frequency components specified by $f_k$ do not have an integer number of cycles over each inspiratory period (see Table 1). Since the mutual orthogonality of the sine and cosine terms of Equations 1 and 2 is guaranteed only over an integer number of cycles, the inspiratory flow and pressure signals approximated by Equations 1 and 2 will not necessarily be projected on an orthonormal basis. In principal this can lead to covariabililty among the least squares estimates of the trigonometric coefficients. However, it was discovered that the off-diagonal elements of the $X^T X$ matrices for flow and pressure were 2–3 orders of magnitude smaller than the diagonal elements, with condition numbers of 22 and 19, respectively. The $X^T X$ matrix is proportional to the covariance matrix, and low condition numbers reflect insignificant covariablity among the elements of $\Theta$.

Implications for Mechanical Ventilation

Although the above-described embodiment relies on a custom-built ventilator system to deliver the EVW to patients, the inspiratory flow pattern of this waveform is simple enough such that most conventional microprocessor-controlled ventilators could easily be programmed to deliver it. Assuming that appropriate compensation techniques are used to correct for the impedance of the ventilator breathing circuit, the EVW and WLS analysis can provide the clinician with a powerful diagnostic tool to assess respiratory function without interruption of mechanical ventilation or additional instrumentation beyond that of the ventilator unit.

While initial motivation for the EVW was to develop a clinically practical technique to measure $Z^{insp}$ in ventilator-dependent patients, the presence of high frequency sinusoids in this waveform may also have a directly beneficial effect on ventilation. A study in rats by Harf et al., Harf, A., R. Le Gall, and H. K. Chang, "Mechanical ventilation with superimposed high frequency oscillation in the normal rat", *Respir. Physiol.* 54: 31–40, 1983, demonstrated that superimposing high frequency oscillations on conventional mechanical ventilation improved ventilation-perfusion homogeneity compared to conventional ventilation alone. Prior to this, Fredberg offered the theory of augmented diffusion in the central airways to explain why high frequency ventilation can maintain normal gas exchange. Fredberg, J. J., "Augmented diffusion in the airways can support pulmonary gas exchange", *J. Appl, Physiol.* 49: 232–238, 1980. It is therefore believed that the high frequency components of the EVW can enhance gas transport, ventilation distribution, or arterial $O_2$ saturation in humans, and is therefore applicable as a therapeutic instrument.

Arising from the fact that data is collected only during inspiration, and expiration is natural, the time period for expiration can last as long (or as short) as needed. Thus, the present invention offers the advantage of a variable inspiratory-period-to-expiratoryperiod ratio. This is especially helpful for patients suffering from disorders that affect the durations of inspiration and expiration.

Conclusion

Together, the EVW and WLS inspiratory analyses have the potential to be a clincally efficient and practical method to measure inspiratory impedance over low frequencies in ventilator-dependent patients without interrupting mechanical ventilation. This inspiratory impedance can be an alternative and useful index to assess the degree and distribution of airway obstruction in patients with flow limitation.

While this invention has been particularly shown and described with references to preferred embodiments thereof, it will be understood by those skilled in the art that various changes in form and detail may be made herein without departing from the spirit and scope of the invention as defined by the appended claims.

We claim:

1. A method for estimating the frequency dependence of respiratory impedance in a patient comprising:
    generating a ventilation function comprising an inspiratory waveform formed by a plurality of energy waves at predetermined frequencies;
    estimating flow and pressure data during delivery of the ventilation function to the patient;
    generating flow and pressure waveforms from the estimated flow and pressure data;
    calculating frequency components in the flow and pressure waveforms at each predetermined frequency; and
    calculating a respiratory impedance estimate at each predetermined frequency based on the flow and pressure waveforms.

2. The method of claim 1 wherein the respiratory impedance estimate includes estimates of resistance and elastance components.

3. The method of claim 1 wherein estimating comprises measuring pressure and flow data at delivery apparatus delivering the ventilation function.

4. The method of claim 1 wherein estimating comprises measuring pressure and flow data at input to the respiratory system of the patient.

5. The method of claim 1 wherein the frequency components of the flow and pressure waveforms comprise amplitude and phase.

6. The method of claim 1 wherein calculating frequency components comprises calculating frequency components in the flow and pressure waveforms at each predetermined frequency using time-weighted linear regression.

7. The method of claim 1 wherein calculating frequency components is performed in the time domain, and wherein the flow and pressure waveforms are time-domain waveforms.

8. The method of claim 7 wherein each time-domain flow and pressure waveform comprises a sum of sine waves of the predetermined frequencies.

9. The method of claim 1 wherein calculating a respiratory impedance estimate comprises calculating impedance at each predetermined frequency as a ratio of the pressure and flow waveforms.

10. The method of claim 1 further comprising selecting the predetermined frequencies according to no-sum-no-difference criteria.

11. The method of claim 1 further comprising selecting the plurality of energy waves to have magnitudes that are chosen to ensure sufficient signal-to-noise in a resulting estimate.

12. The method of claim 1 further comprising selecting the plurality of energy waves to have phases that are chosen such that a resulting ventilation function delivers sufficient fluid volume to maintain ventilation.

13. The method of claim 1 further comprising following each inspiration, isolating the patient from the ventilation function to allow for natural expiration.

14. The method of claim 13 wherein the inspiration time duration and expiration time duration are different.

15. The method of claim 1 wherein the predetermined frequencies are within a range of 0.1 Hz and 8 Hz.

16. The method of claim 15 further comprising applying high-frequency components to the ventilation function to provide for a therapeutic effect.

17. The method of claim 1 wherein generating flow and pressure waveforms from the estimated flow and pressure data is based exclusively on flow and pressure data collected during inspiration.

18. The method of claim 1 wherein calculating frequency components in the flow and pressure waveforms at each predetermined frequency is based exclusively on flow and pressure data collected during inspiration.

19. The method of claim 1 wherein calculating a respiratory impedance estimate at each predetermined frequency based on the flow and pressure waveforms is based exclusively on flow and pressure data collected during inspiration.

20. A system for estimating the frequency dependence of respiratory impedance in a patient comprising:
    a ventilation function generator for generating a ventilation function comprising an inspiratory waveform formed by a plurality of energy waves at predetermined frequencies;
    a flow and pressure estimator for estimating flow and pressure data during delivery of the ventilation function to the patent;
    a waveform generator for generating flow and pressure waveforms from the estimated flow and pressure data; and
    a data processor for:
        calculating frequency components in the flow and pressure waveforms at each predetermined frequency; and
        calculating a respiratory impedance estimate at each predetermined frequency based on the flow and pressure waveforms.

21. The system of claim 20 wherein the respiratory impedance estimate includes estimates of resistance and elastance components.

22. The system of claim 20 wherein the flow and pressure estimator measures pressure and flow data at the delivery apparatus delivering the ventilation function.

23. The system of claim 20 wherein the flow and pressure estimator measures pressure and flow data at input to the respiratory system of the patient.

24. The system of claim 20 wherein the frequency components of the flow and pressure waveforms comprise amplitude and phase.

25. The system of claim 20 wherein the data processor calculates frequency components in the flow and pressure waveforms at each predetermined frequency using time-weighted linear regression.

26. The system of claim 20 wherein the data processor calculates frequency components in the flow and pressure waveforms at each predetermined frequency in the time domain, and wherein the flow and pressure waveforms are time-domain waveforms.

27. The system of claim 26 wherein each time-domain flow and pressure waveform comprises a sum of sine waves of the predetermined frequencies.

28. The system of claim 20 wherein the data processor calculates an impedance estimate at each predetermined frequency as a ratio of the pressure and flow waveforms.

29. The system of claim 20 wherein the predetermined frequencies are selected according to no-sum-no-difference criteria.

30. The system of claim 20 wherein the energy waves have magnitudes that are chosen to ensure sufficient signal-to-noise in the resulting estimate.

31. The system of claim 20 wherein the energy waves have phases that are chosen such that the resulting ventilation function delivers sufficient fluid volume to maintain ventilation.

32. The system of claim 20 further comprising means for isolating the patent from the ventilation function following each inspiration to allow for natural expiration.

33. The system of claim 32 wherein the inspiration time duration and expiration time duration are different.

34. The system of claim 20 wherein the predetermined frequencies are within a range of 0.1 Hz and 8 Hz.

35. The system of claim 34 wherein high-frequency components are applied to the ventilation function.

36. The system of claim 20 wherein the generation of flow and pressure waveforms from the estimated flow and pressure data is based exclusively on flow and pressure data collected during inspiration.

37. The system of claim 20 wherein the calculation of frequency components in the flow and pressure waveforms at each predetermined frequency is based exclusively on flow and pressure data collected during inspiration.

38. The system of claim 20 wherein the calculation of a respiratory impedance estimate at each predetermined frequency based on the flow and pressure waveforms is based exclusively on flow and pressure data collected during. inspiration.

* * * * *